(12) United States Patent
Shojaei et al.

(10) Patent No.: US 11,864,970 B2
(45) Date of Patent: Jan. 9, 2024

(54) ACCURATE METHOD TO DETERMINE CENTER OF RESISTANCE FOR 1D/2D/3D PROBLEMS

(71) Applicant: ALIGN TECHNOLOGY, INC., San Jose, CA (US)

(72) Inventors: Iman Shojaei, Sunnyvale, CA (US); Reza Shirazi Aghjari, San Jose, CA (US); John Y. Morton, San Jose (CA) (US); Vadim Matov, San Jose, CA (US); Eric Yau, Santa Clara, CA (US); Fuming Wu, Pleasanton, CA (US); Sergei Brodsky, San Jose, CA (US)

(73) Assignee: ALIGN TECHNOLOGY, INC., San Jose, CA (US)

( * ) Notice: Subject to any disclaimer, the term of this patent is extended or adjusted under 35 U.S.C. 154(b) by 0 days.

(21) Appl. No.: 17/453,591

(22) Filed: Nov. 4, 2021

(65) Prior Publication Data

US 2022/0142740 A1 May 12, 2022

Related U.S. Application Data

(60) Provisional application No. 63/110,864, filed on Nov. 6, 2020.

(51) Int. Cl.
*A61C 7/00* (2006.01)
*G16H 20/40* (2018.01)
*G16H 50/50* (2018.01)

(52) U.S. Cl.
CPC .............. *A61C 7/002* (2013.01); *G16H 20/40* (2018.01); *G16H 50/50* (2018.01); *A61C 2007/004* (2013.01)

(58) Field of Classification Search
CPC ..... A61C 7/002; A61C 2007/004; A61C 7/08; G16H 20/40; G16H 50/50; G16H 20/00; G16H 30/00; G16H 30/40; A61B 6/461; A61B 6/466; A61B 6/5211; A61B 34/10; B01J 2219/0095; B25J 9/1605; G01N 29/4472; G05B 2219/40321
See application file for complete search history.

(56) References Cited

U.S. PATENT DOCUMENTS 5,975,893 A 11/1999 Chishti et al.
6,227,850 B1 5/2001 Chishti et al.
6,227,851 B1 5/2001 Chishti et al.
(Continued)

*Primary Examiner* — Jacqueline T Johanas
*Assistant Examiner* — Lina Faraj
(74) *Attorney, Agent, or Firm* — FISHERBROYLES, LLP

(57) ABSTRACT

A system and method for determining a center of resistance of a tooth may include receiving a 3D digital representation of an initial arrangement and a final arrangement of a patient's teeth and determining a 3D treatment plan. The 3D treatment plan may include a plurality of 3D stages for rearranging the teeth from the initial arrangement toward the final arrangement. The method may also include determining, in accordance with the 3D treatment plan, an intended movement of the teeth for each of the stages and deriving, using a 3D resistance model, an applied force system for achieving the intended movement of the teeth for each of the stages. The method may also include deriving 3D geometries of oral appliances for the stages in response to the applied force system. Various other systems and methods are also disclosed.

8 Claims, 15 Drawing Sheets

(56) References Cited

U.S. PATENT DOCUMENTS

| | | |
|---|---|---|
| 6,299,440 B1 | 10/2001 | Phan et al. |
| 6,309,215 B1 | 10/2001 | Phan et al. |
| 6,318,994 B1 | 11/2001 | Chishti et al. |
| 6,371,761 B1 | 4/2002 | Cheang et al. |
| 6,386,878 B1 | 5/2002 | Pavlovskaia et al. |
| 6,406,292 B1 | 6/2002 | Chishti et al. |
| 6,409,504 B1 | 6/2002 | Jones et al. |
| 6,450,807 B1 | 9/2002 | Chishti et al. |
| 6,457,972 B1 | 10/2002 | Chishti et al. |
| 6,488,499 B1 | 12/2002 | Miller |
| 6,514,074 B1 | 2/2003 | Chishti et al. |
| 6,554,611 B2 | 4/2003 | Chishti et al. |
| 6,582,229 B1 | 6/2003 | Miller et al. |
| 6,602,070 B2 | 8/2003 | Miller et al. |
| 6,621,491 B1 | 9/2003 | Baumrind et al. |
| 6,688,886 B2 | 2/2004 | Hughes et al. |
| 6,726,478 B1 | 4/2004 | Isiderio et al. |
| 6,729,876 B2 | 5/2004 | Chishti et al. |
| 6,739,869 B1 | 5/2004 | Taub et al. |
| 6,767,208 B2 | 7/2004 | Kaza |
| 6,783,360 B2 | 8/2004 | Chishti |
| 6,830,450 B2 | 12/2004 | Knopp et al. |
| 7,040,896 B2 | 5/2006 | Pavlovskaia et al. |
| 7,063,532 B1 | 6/2006 | Jones et al. |
| 7,074,038 B1 | 7/2006 | Miller |
| 7,074,039 B2 | 7/2006 | Kopelman et al. |
| 7,077,647 B2 | 7/2006 | Choi et al. |
| 7,108,508 B2 | 9/2006 | Hedge et al. |
| 7,134,874 B2 | 11/2006 | Chishti et al. |
| 7,156,661 B2 | 1/2007 | Choi et al. |
| 7,160,107 B2 | 1/2007 | Kopelman et al. |
| 7,241,142 B2 | 7/2007 | Abolfathi et al. |
| 7,293,988 B2 | 11/2007 | Wen |
| 7,309,230 B2 | 12/2007 | Wen |
| 7,357,634 B2 | 4/2008 | Knopp |
| 7,555,403 B2 | 6/2009 | Kopelman et al. |
| 7,637,740 B2 | 12/2009 | Knopp |
| 7,689,398 B2 | 3/2010 | Cheng et al. |
| 7,736,147 B2 | 6/2010 | Kaza et al. |
| 7,746,339 B2 | 6/2010 | Matov et al. |
| 7,844,356 B2 | 11/2010 | Matov et al. |
| 7,844,429 B2 | 11/2010 | Matov et al. |
| 7,865,259 B2 | 1/2011 | Kuo et al. |
| 7,878,804 B2 | 2/2011 | Korytov et al. |
| 7,880,751 B2 | 2/2011 | Kuo et al. |
| 7,904,308 B2 | 3/2011 | Arnone et al. |
| 7,930,189 B2 | 4/2011 | Kuo |
| 7,942,672 B2 | 5/2011 | Kuo |
| 7,970,627 B2 | 6/2011 | Kuo et al. |
| 7,970,628 B2 | 6/2011 | Kuo et al. |
| 8,038,444 B2 | 10/2011 | Kitching et al. |
| 8,044,954 B2 | 10/2011 | Kitching et al. |
| 8,075,306 B2 | 12/2011 | Kitching et al. |
| 8,092,215 B2 | 1/2012 | Stone-Collonge et al. |
| 8,099,268 B2 | 1/2012 | Kitching et al. |
| 8,108,189 B2 | 1/2012 | Chelnokov et al. |
| 8,126,726 B2 | 2/2012 | Matov et al. |
| 8,260,591 B2 | 9/2012 | Kass et al. |
| 8,275,180 B2 | 9/2012 | Kuo |
| 8,401,826 B2 | 3/2013 | Cheng et al. |
| 8,439,672 B2 | 5/2013 | Matov et al. |
| 8,562,338 B2 | 10/2013 | Kitching et al. |
| 8,591,225 B2 | 11/2013 | Wu et al. |
| 8,788,285 B2 | 7/2014 | Kuo |
| 8,843,381 B2 | 9/2014 | Kuo et al. |
| 8,874,452 B2 | 10/2014 | Kuo |
| 8,896,592 B2 | 11/2014 | Boltunov et al. |
| 8,930,219 B2 | 1/2015 | Trosien et al. |
| 9,037,439 B2 | 5/2015 | Kuo et al. |
| 9,060,829 B2 | 6/2015 | Sterental et al. |
| 9,125,709 B2 | 9/2015 | Matty |
| 9,211,166 B2 | 12/2015 | Kuo et al. |
| 9,220,580 B2 | 12/2015 | Borovinskih et al. |
| 9,364,296 B2 | 6/2016 | Kuo |
| 9,375,300 B2 | 6/2016 | Matov et al. |
| 9,414,897 B2 | 8/2016 | Wu et al. |
| 9,492,245 B2 | 11/2016 | Sherwood et al. |
| 9,642,678 B2 | 5/2017 | Kuo |
| 10,248,883 B2 | 4/2019 | Borovinskih et al. |
| 10,342,638 B2 | 7/2019 | Kitching et al. |
| 10,463,452 B2 | 11/2019 | Matov et al. |
| 10,595,966 B2 | 3/2020 | Carrier, Jr. et al. |
| 10,617,489 B2 | 4/2020 | Grove et al. |
| 10,722,328 B2 | 7/2020 | Velazquez et al. |
| 10,758,322 B2 | 9/2020 | Pokotilov et al. |
| 10,779,718 B2 | 9/2020 | Meyer et al. |
| 10,792,127 B2 | 10/2020 | Kopelman et al. |
| 10,828,130 B2 | 11/2020 | Pokotilov et al. |
| 10,835,349 B2 | 11/2020 | Cramer et al. |
| 10,856,954 B1* | 12/2020 | Raslambekov ........ A61C 19/04 |
| 10,973,611 B2 | 4/2021 | Pokotilov et al. |
| 10,996,813 B2 | 5/2021 | Makarenkova et al. |
| 10,997,727 B2 | 5/2021 | Xue et al. |
| 11,020,206 B2 | 6/2021 | Shi et al. |
| 11,026,766 B2 | 6/2021 | Chekh et al. |
| 11,033,359 B2 | 6/2021 | Velazquez et al. |
| 11,071,608 B2 | 7/2021 | Derakhshan et al. |
| 11,096,763 B2 | 8/2021 | Akopov et al. |
| 11,116,605 B2 | 9/2021 | Nyukhtikov et al. |
| 11,147,652 B2 | 10/2021 | Mason et al. |
| 11,151,753 B2 | 10/2021 | Gao et al. |
| 11,259,896 B2 | 3/2022 | Matov et al. |
| 11,278,376 B1* | 3/2022 | Wucher ................ A61B 5/0053 |
| 11,298,211 B2* | 4/2022 | Boronkay ................ A61C 7/14 |
| 11,517,400 B1* | 12/2022 | Raslambekov ........ G16H 20/40 |
| 2003/0008259 A1 | 1/2003 | Kuo et al. |
| 2003/0143509 A1 | 7/2003 | Kopelman et al. |
| 2003/0207227 A1 | 11/2003 | Abolfathi |
| 2004/0137400 A1 | 7/2004 | Chishti et al. |
| 2004/0152036 A1 | 8/2004 | Abolfathi |
| 2004/0197728 A1 | 10/2004 | Abolfathi et al. |
| 2004/0259049 A1 | 12/2004 | Kopelman et al. |
| 2005/0182654 A1 | 8/2005 | Abolfathi et al. |
| 2005/0244791 A1 | 11/2005 | Davis et al. |
| 2006/0127836 A1 | 6/2006 | Wen |
| 2006/0127852 A1 | 6/2006 | Wen |
| 2006/0127854 A1 | 6/2006 | Wen |
| 2006/0275731 A1 | 12/2006 | Wen et al. |
| 2006/0275736 A1 | 12/2006 | Wen et al. |
| 2008/0306724 A1 | 12/2008 | Kitching et al. |
| 2008/0311535 A1* | 12/2008 | Andreiko ................ A61C 7/12 433/24 |
| 2010/0009308 A1 | 1/2010 | Wen et al. |
| 2010/0068672 A1 | 3/2010 | Arjomand et al. |
| 2010/0068676 A1 | 3/2010 | Mason et al. |
| 2010/0092907 A1 | 4/2010 | Knopp |
| 2010/0167243 A1 | 7/2010 | Spiridonov et al. |
| 2013/0204599 A1* | 8/2013 | Matov .................... G16H 50/50 703/11 |
| 2016/0310235 A1 | 10/2016 | Derakhshan et al. |
| 2017/0007365 A1 | 1/2017 | Kopelman et al. |
| 2017/0273760 A1 | 9/2017 | Morton et al. |
| 2018/0280118 A1 | 10/2018 | Cramer |
| 2019/0000593 A1* | 1/2019 | Cam .................... A61C 7/282 |
| 2019/0029784 A1 | 1/2019 | Moalem et al. |
| 2019/0053876 A1 | 2/2019 | Sterental et al. |
| 2019/0192259 A1 | 6/2019 | Kopelman et al. |
| 2019/0328487 A1 | 10/2019 | Levin et al. |
| 2019/0328488 A1 | 10/2019 | Levin et al. |
| 2019/0333622 A1 | 10/2019 | Levin et al. |
| 2019/0343601 A1 | 11/2019 | Roschin et al. |
| 2020/0000551 A1 | 1/2020 | Li et al. |
| 2020/0000552 A1 | 1/2020 | Mednikov et al. |
| 2020/0000554 A1 | 1/2020 | Makarenkova et al. |
| 2020/0000555 A1 | 1/2020 | Yuryev et al. |
| 2020/0085546 A1 | 3/2020 | Li et al. |
| 2020/0107915 A1 | 4/2020 | Roschin et al. |
| 2020/0155274 A1 | 5/2020 | Pimenov et al. |
| 2020/0214800 A1 | 7/2020 | Matov et al. |
| 2020/0297458 A1 | 9/2020 | Roschin et al. |
| 2020/0306010 A1* | 10/2020 | Aamodt .................... G06T 7/38 |
| 2020/0306011 A1 | 10/2020 | Chekhonin et al. |
| 2020/0306012 A1 | 10/2020 | Roschin et al. |
| 2020/0315744 A1 | 10/2020 | Cramer |

(56) References Cited

U.S. PATENT DOCUMENTS

| | | |
|---|---|---|
| 2020/0360109 A1 | 11/2020 | Gao et al. |
| 2020/0375698 A1* | 12/2020 | Paehl ........................ A61C 7/08 |
| 2021/0073998 A1 | 3/2021 | Brown et al. |
| 2021/0134436 A1 | 5/2021 | Meyer et al. |
| 2021/0174477 A1 | 6/2021 | Shi et al. |
| 2022/0401185 A1* | 12/2022 | Boronkay ................ A61C 7/14 |

* cited by examiner

1D Problem

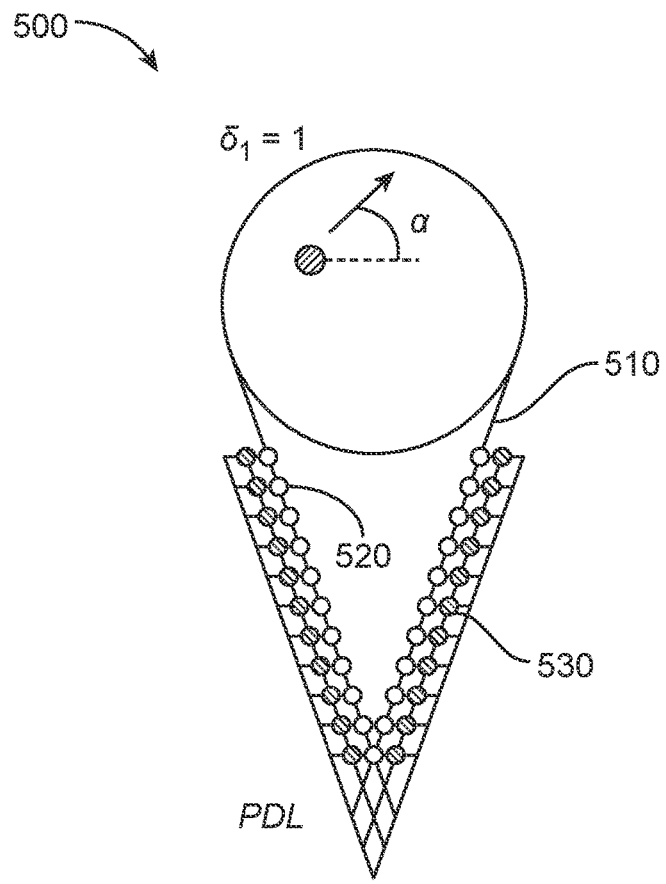

FIG. 5A $$\begin{bmatrix} f_{x_1} \\ f_{y_1} \\ f_{x_2} \\ f_{y_2} \\ \vdots \\ f_{x_i} \\ f_{y_i} \\ \vdots \end{bmatrix} = \begin{bmatrix} H_{11} & H_{12} & H_{13} & H_{14} & \cdots & H_{1i} & H_{1,i+1} & \cdots \\ H_{21} & H_{22} & H_{23} & H_{24} & \cdots & H_{2i} & H_{2,i+1} & \cdots \\ H_{31} & H_{32} & H_{33} & H_{34} & \cdots & H_{3i} & H_{3,i+1} & \cdots \\ H_{41} & H_{42} & H_{43} & H_{44} & \cdots & H_{4i} & H_{4,i+1} & \cdots \\ \vdots & \vdots & \vdots & \vdots & \ddots & \vdots & \vdots & \cdots \\ H_{i1} & H_{i2} & H_{i3} & H_{i4} & \cdots & H_{ii} & H_{i,i+1} & \cdots \\ H_{i+1,1} & H_{i+1,2} & H_{i+1,3} & H_{i+1,4} & \cdots & H_{i+1,i} & H_{i+1,i+1} & \cdots \\ \vdots & \vdots & \vdots & \vdots & & \vdots & \vdots & \ddots \end{bmatrix} \begin{bmatrix} \cos \alpha \\ \sin \alpha \\ \cos \alpha \\ \sin \alpha \\ \vdots \\ \cos \alpha \\ \sin \alpha \\ \vdots \end{bmatrix}$$

FIG. 5B

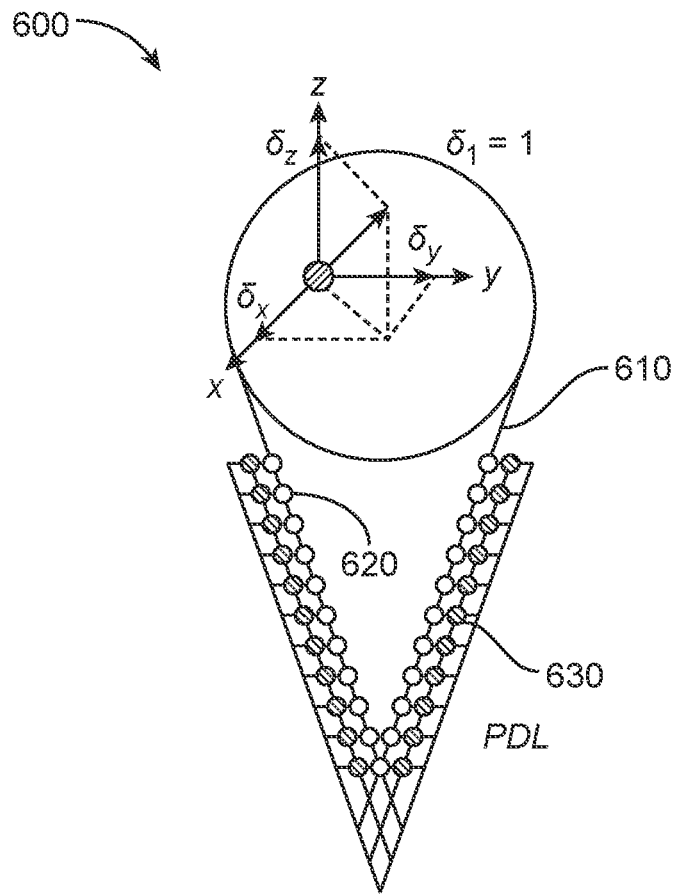

FIG. 6A $$\begin{bmatrix} f_{x_1} \\ f_{y_1} \\ f_{z_1} \\ \vdots \\ f_{x_i} \\ f_{y_i} \\ f_{z_i} \\ \vdots \end{bmatrix} = \begin{bmatrix} H_{11} & H_{12} & H_{13} & H_{14} & \cdots & H_{1i} & H_{1,i+1} & \cdots \\ H_{21} & H_{22} & H_{23} & H_{24} & \cdots & H_{2i} & H_{2,i+1} & \cdots \\ H_{31} & H_{32} & H_{33} & H_{34} & \cdots & H_{3i} & H_{3,i+1} & \cdots \\ H_{41} & H_{42} & H_{43} & H_{44} & \cdots & H_{4i} & H_{4,i+1} & \cdots \\ \vdots & \vdots & \vdots & \vdots & \ddots & \vdots & \vdots & \cdots \\ H_{i1} & H_{i2} & H_{i3} & H_{i4} & \cdots & H_{ii} & H_{i,i+1} & \cdots \\ H_{i+1,1} & H_{i+1,2} & H_{i+1,3} & H_{i+1,4} & \cdots & H_{i+1,i} & H_{i+1,i+1} & \cdots \\ \vdots & \vdots & \vdots & \vdots & \vdots & \vdots & \vdots & \ddots \end{bmatrix} \begin{bmatrix} \delta_x \\ \delta_y \\ \delta_z \\ \vdots \\ \delta_x \\ \delta_y \\ \delta_z \\ \vdots \end{bmatrix}$$

FIG. 6B

ACCURATE METHOD TO DETERMINE CENTER OF RESISTANCE FOR 1D/2D/3D PROBLEMS

RELATED APPLICATIONS

This application claims the benefit under 35 U.S.C. § 119(e) of U.S. Provisional Patent Application No. 63/110,864, filed Nov. 6, 2020, and titled "ACCURATE METHOD TO DETERMINE CENTER OF RESISTANCE FOR 1D/2D/3D PROBLEMS," which is incorporated, in its entirety, by this reference.

BACKGROUND

Prior approaches to orthodontic and dental treatment such as repositioning teeth can be less than ideal in at least some respects. Treatment planning may involve various steps before an appropriate oral appliance is fabricated for the patient, and patient records and other data may be collected. For example, data on the patient's mouth may be acquired by scanning the mouth directly or with impressions of the mouth. Once the patient's mouth has been digitized, a practitioner may plan out final teeth positions to treat the patient. Although software tools may aid during the design process, such tools may rely on in accurate assumptions. In at least some instances, the software tools may rely on an inaccurate location of a center of resistance (CoR) of the patient's teeth to model tooth movement, which can result in inaccurate and undesirable tooth movements.

A patient's treatment plan may rely on oral appliances that are placed on the teeth sequentially to provide incremental movement in order to complete a treatment, which may span months. In at least some instances, a patient may decide to discontinue treatment part way through the treatment, which may be related to the teeth not moving correctly at each of the stages. For example, at later stages of the treatment the appliance may become difficult for the patient to place on the teeth, and the patient may experience some discomfort when one or more teeth do not move in accordance with the treatment plan. Although the steps of scanning the patient's dentition and generating a new set of appliances could be repeated, this could result in an inconvenience for the patient and treatment professional. Work in relation to the present disclosure suggests that one or more teeth not moving in accordance to the treatment plan may be related to less than ideal modeling of the movement of the teeth at the various stages and associated forces.

Prior approaches to modeling tooth movement may be less than ideal in at least some respects. For example, the center of resistance (CoR) may not have been adequately addressed with prior treatment modeling, which can result in deviation of the actual tooth movement in relation to the intended tooth movement. Work in relation to the present disclosure suggests that these deviations in tooth movement from the intended treatment plan may be related to incorrect assumptions regarding the CoR in at least some instances. For example, prior approaches to treatment planning may rely on a CoR of the tooth that differs from the actual CoR and this difference can vary, which can result in less than ideal outcomes in at least some instances. For instance, some prior approaches may rely on a center of mass or center of surface to determine the CoR. Another approach has been to assume that the CoR is located approximately 40% of the distance from the alveolar crest to the end of the tooth root. However, these prior approaches do not take into consideration the biomechanical properties of other structures related to the dentition, such as the periodontal ligament (PDL) and properties of the PDL and other tissues, which can affect the location of the CoR by fractions of a millimeter or more in at least some instances. The inaccuracies of these prior approaches with respect to the CoR may result in unintended tooth movements, such as rotations and less than ideal translation in at least some instances.

The prior approaches have also inadequately addressed situations in which the CoR effectively changes in response to the direction of the applied force, which can be related to non-linearities with respect to material properties and associated tooth movements. Examples of types of tooth movements include, intrusions, extrusions, rotations, mesial movement, distal movement and buccal movement, and the CoR can effectively change depending on the orientations of the applied forces. In at least some instances, the location of a tooth through which a force will result in only translation of the tooth, e.g. without rotation, can change significantly such that the CoR can be considered non-existent. For example, as the direction of desired tooth movement changes, the location on the tooth that provides only translation may vary by an amount approaching a millimeter or more.

Although finite element modeling has been proposed to model force and movement of a tooth, the prior approaches to finite element modeling can be computationally intensive and may not be well suited for use with all of the steps and stages involved with treatment planning in at least some instances.

In light of the above, there is a need for treatments and planning that ameliorate at least some of the aforementioned limitations of the prior oral approaches. Ideally, such approaches would more accurately predict tooth movement, improve appliance designs, decrease unwanted deviations from the intended treatment plan, decrease computational resources used, and allow more patients to complete treatment.

SUMMARY

The presently disclosed systems and methods provide improved treatment planning and outcomes with improved tooth movements related to center of resistance data. In some embodiments, derived center of resistance data is used for each treated tooth over a plurality of treatment stages, which may improve outcomes and reduce a number of changes or revisions to the treatment plan during the treatment process. In some embodiments, various systems and methods for digital treatment planning rely on the identified location of the tooth that provides only translation in response to the direction of displacement for each stage of a plurality of stages, so as to provide improved modeling of the force systems, tooth movements, and appliance shapes to move the tooth toward an intended position at each of the plurality of stages. In some embodiments, the location of a force applied to the tooth that provides only translation is substantially independent of the orientation of the intended displacement, such that the center of resistance exists and defines the location of the tooth that provides only translation, which can be used for modeling movement of the tooth at a stage of treatment. Alternatively or in combination, the location of a force applied the tooth that provides only translation can be substantially dependent of the orientation of the intended displacement at a stage of treatment, such that the center of resistance does not exist and the location on the tooth that provides only translation at the orientation of the displacement is used to model the movement of the tooth. By using a three-dimensional (3D) resistance model of teeth incorporating improved center of resistance data and identified locations that provide only translation for the orientation of the displacement, the systems and methods described herein may provide a more accurate approach to configuring oral appliances to achieve the intended tooth movement.

In addition, the systems and methods described herein may improve the functioning of a computing device by more efficiently modeling biomechanical tooth movement to reduce processing overhead of complicated simulations and producing reusable data points. These systems and methods may also improve the field of oral appliance design by producing oral appliance geometries that may more reliably achieve intended tooth movement. In some embodiments, finite element modeling can be used to determine lines of resistance of a tooth for a portion of the treatment so as to decrease computational resources and decrease the amount of time to generate a treatment plan. Also, the center of resistance of a tooth, once determined, can decrease the computational resources used and increase the speed at which a treatment plan is derived. In some embodiments, finite element modeling can be used with a simplified surface of the tooth, such as a conic surface of appropriate dimensions so as to decrease computational resources.

In some embodiments, a database of treatments derived from tooth specific CoR data comprises an initial configuration of teeth, a final configuration of the teeth, intended displacements for a plurality of stages and corresponding forces and/or appliance shapes, and outcome metrics, such as the percentage of patients completing treatment and deviations from the intended treatment. The treatment planning processor can be configured to receive an initial configuration of teeth and a final intended configuration of teeth as inputs, access the database, identify similar initial and final configurations of teeth corresponding to successful treatments, and output a treatment plan comprising a plurality of stages and tooth movements corresponding to the successful treatments. Utilizing a database of treatments derived from CoR data has the advantage of decreasing computational time and complexity, while providing a treatment plan similar to successful treatment plans based on CoR data. While the treatment planning software instructions can be configured in many ways, in some embodiments, a look up table or pick table is configured to identify a closest successful treatment in response to the input initial tooth configuration and the final intended tooth configuration.

INCORPORATION BY REFERENCE

All patents, applications, and publications referred to and identified herein are hereby incorporated by reference in their entirety and shall be considered fully incorporated by reference even though referred to elsewhere in the application.

BRIEF DESCRIPTION OF THE DRAWINGS

A better understanding of the features, advantages and principles of the present disclosure will be obtained by reference to the following detailed description that sets forth illustrative embodiments, and the accompanying drawings of which:

FIG. 5A shows a mathematical model for modeling a tooth as a two-dimensional (2D) model, in accordance with some embodiments;

FIG. 5B illustrates a stiffness matrix, in accordance with some embodiments;

FIG. 6A shows a mathematical model for modeling a tooth as a three-dimensional (3D) model, in accordance with some embodiments;

FIG. 6B illustrates a 3D stiffness matrix, in accordance with some embodiments;

DETAILED DESCRIPTION

Figure 1A:
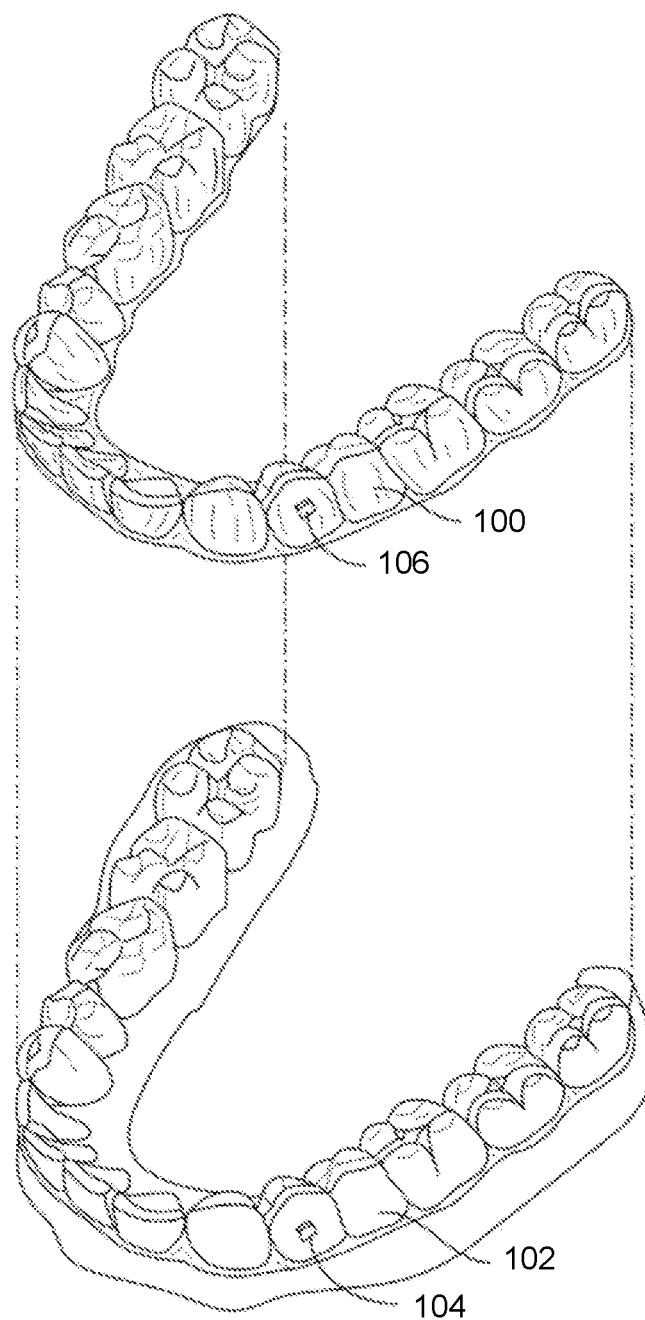
FIG. 1A illustrates an exemplary tooth repositioning appliance or aligner that can be worn by a patient in order to achieve an incremental repositioning of individual teeth in the jaw, in accordance with some embodiments.

The following detailed description and provides a better understanding of the features and advantages of the inventions described in the present disclosure in accordance with the embodiments disclosed herein. Although the detailed description includes many specific embodiments, these are provided by way of example only and should not be construed as limiting the scope of the inventions disclosed herein.

As will be described further below, the systems and methods provided in this disclosure may utilize mathematically derived models to optimize appliance design. The systems and methods provided in this disclosure may improve the functioning of a computing device by producing more accurate designs without requiring significantly more data or complex calculations, which may further reduce storage requirements and processing overhead. In addition, the systems and methods provided herein may improve the field of orthodontic care by improving the initial treatment plans and appliance designs. Moreover, the systems and methods provided herein may improve the field of biomechanical modeling by using more accurate modeling systems.

In some embodiments, the presently disclosed systems and methods provide improved teeth repositioning determining lines of resistance and the corresponding CoR in response to the angles of a force vector applied to one or more teeth. The lines of resistance and corresponding translational force systems, moments and couplings to move teeth as described herein can be used to determine the shape of appliances to more effectively move teeth with fewer unwanted or undesirable tooth movements. Alternatively or in combination, the treatments and outcomes may be incorporated into a databased of treatments that can be used to more accurately predict tooth movements and plan treatments.

The CoR of a tooth may be used to simulate how applied forces may move the tooth in a biomechanical model of a mouth. In other words, the CoR may indicate a point where a single force applied produces pure tooth translation in the direction of the applied force. However, work in relation to the present disclosure suggests that a 3D CoR may not exist for all teeth, because the location of the tooth that provides only translation with a force applied to it can change based on the orientation of the desired tooth displacement. The presently disclosed systems and methods can rely on a more accurate determination of the CoR, if present, and a location of the tooth that provides only translation for a displacement vector, so as to provide improved treatments.

The location of CoR of teeth may be helpful in designing orthodontic appliances such as aligners. Small deviations from the actual location of CoR may result in undesired forces, leading to unwanted clinical outcomes such as unwanted movements. As described herein, the systems and methods described herein may use accurate CoR determinations as the basis of force systems that may be programmed into the treatment planning software as a set of clinical treatment protocols that may not explicitly use the force systems but rather use displacement systems corresponding to the force systems. Alternatively or in addition, the systems and methods described herein may use accurate CoR determinations as the basis of force systems that are calculated during the course of treatment planning as part of treatment planning software while using clinical treatment protocols that modify displacements with modified force systems.

The systems and methods described herein may use more accurate CoR calculations using principles of linear/nonlinear structural mechanics and mathematics that may be applied to 1D/2D/3D geometrical bodies with discreet/continuous surrounding constraints, including teeth-PDL-bone. In addition, the systems and methods described herein may use CoR estimations in circumstances where CoR may not be feasibly determined. The systems and methods described herein may provide a solution for any translations and/or rotations, which may result in consistent desired clinical outcomes. The systems and methods described herein may also provide adjustable parameters, such as one or more of tooth properties and PDL properties, in order to improve appliance design. The systems and methods described herein may also take into account all potential nonlinearities including complex geometries and materials in order to increase predictability of treatment. Thus, an effective appliance may be designed for each stage of a patient's treatment.

Although the examples herein are described with respect to orthodontic care, in other implementations the CoR determinations described herein may be applied to other corrective treatments and other biomechanical scenarios.

The presently disclosed systems and methods are well suited for incorporation with prior approaches to moving teeth, for example as described in U.S. application Ser. No. 15/202,472, entitled "Direct fabrication of aligners with interproximal force coupling", filed on Jul. 5, 2017, published as US20170007365 on Jan. 12, 2017, the entire disclosure of which is incorporated herein by reference.

The following will provide, with reference to FIGS. 1A-12, detailed descriptions of medical imaging, modeling, treatment planning and appliances for treatment. Detailed descriptions of example oral appliances will be provided in connection with FIGS. 1A-1C. Detailed descriptions of exemplary oral appliances using power arms will be provided in connection with FIGS. 2-3. Detailed descriptions of mathematical models for determining CoR will be provided in connection with FIGS. 4A-6B. Detailed descriptions of example computing systems for medical imaging and treatment planning will be provided in connection with FIG. 7. Detailed descriptions of example computing systems for determining CoR will be provided in connection with FIG. 8. Detailed descriptions of corresponding computer-implemented methods will also be provided in connection with FIGS. 9 and 10. In addition, detailed descriptions of an example computing system and network architecture capable of implementing one or more of the embodiments described herein will be provided in connection with FIGS. 11 and 12.

FIG. 1A illustrates an exemplary tooth repositioning appliance 100, such as an aligner that can be worn by a patient in order to achieve an incremental repositioning of individual teeth 102 in the jaw. The appliance can include a shell (e.g., a continuous polymeric shell or a segmented shell) having teeth-receiving cavities that receive and resiliently reposition the teeth. An appliance or portion(s) thereof may be indirectly fabricated using a physical model of teeth. For example, an appliance (e.g., polymeric appliance) can be formed using a physical model of teeth and a sheet of suitable layers of polymeric material. The physical model (e.g., physical mold) of teeth can be formed through a variety of techniques, including 3D printing. The appliance can be formed by thermoforming the appliance over the physical model. In some embodiments, a physical appliance is directly fabricated, e.g., using additive manufacturing techniques, from a digital model of an appliance. In some embodiments, the physical appliance may be created through a variety of direct formation techniques, such as 3D printing. An appliance can fit over all teeth present in an upper or lower jaw, or less than all of the teeth. The appliance can be designed specifically to accommodate the teeth of the patient (e.g., the topography of the tooth-receiving cavities matches the topography of the patient's teeth), and may be fabricated based on positive or negative models of the patient's teeth generated by impression, scanning, and the like. Alternatively, the appliance can be a generic appliance configured to receive the teeth, but not necessarily shaped to match the topography of the patient's teeth. In some cases, only certain teeth received by an appliance will be repositioned by the appliance while other teeth can provide a base or anchor region for holding the appliance in place as it applies force against the tooth or teeth targeted for repositioning. In some cases, some or most, and even all, of the teeth will be repositioned at some point during treatment. Teeth that are moved can also serve as a base or anchor for holding the appliance as it is worn by the patient. In some embodiments, no wires or other means will be provided for holding an appliance in place over the teeth. In some cases, however, it may be desirable or necessary to provide individual attachments or other anchoring elements 104 on teeth 102 with corresponding receptacles or apertures 106 in the appliance 100 so that the appliance can apply a selected force on the tooth. Exemplary appliances, including those utilized in the Invisalign® System, are described in numerous patents and patent applications assigned to Align Technology, Inc. including, for example, in U.S. Pat. Nos. 6,450,807, and 5,975,893, as well as on the company's website, which is accessible on the World Wide Web (see, e.g., the URL "invisalign.com"). Examples of tooth-mounted attachments suitable for use with orthodontic appliances are also described in patents and patent applications assigned to Align Technology, Inc., including, for example, U.S. Pat. Nos. 6,309,215 and 6,830,450.

Figure 1B:
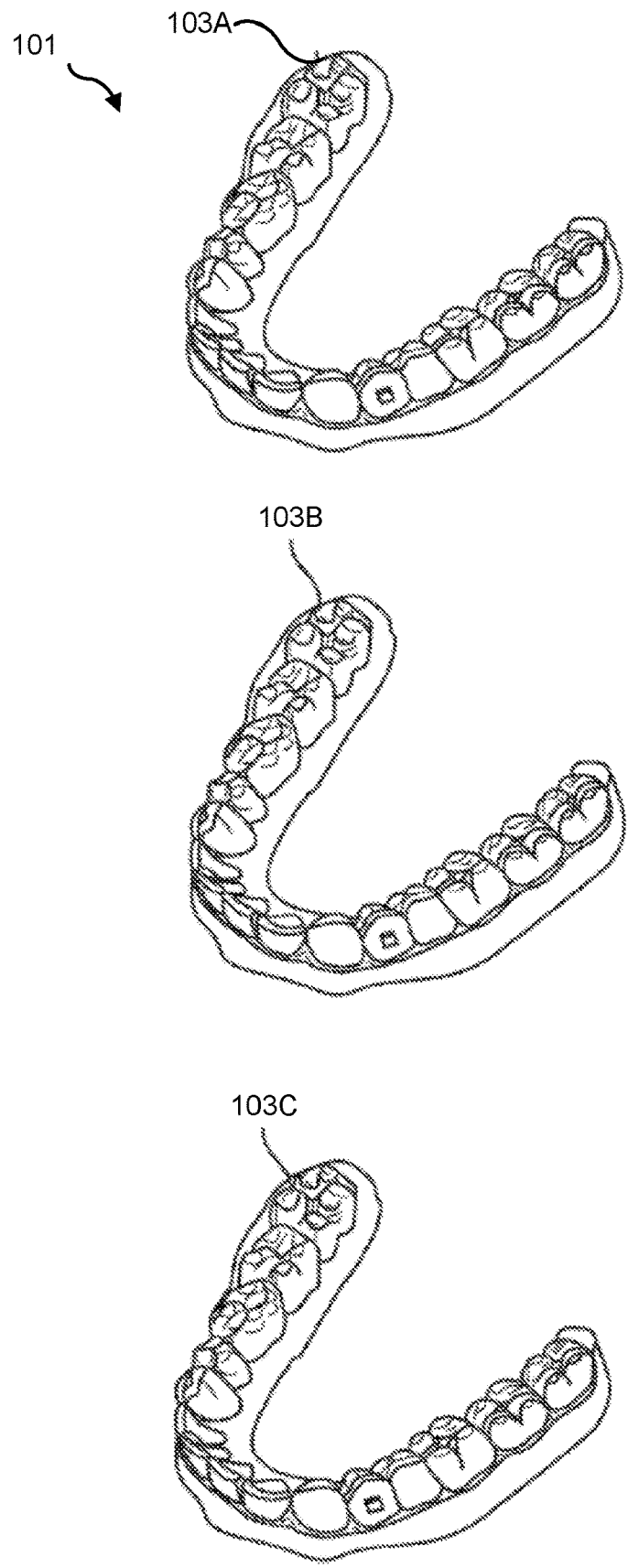
FIG. 1B illustrates a tooth repositioning system, in accordance with some embodiments.

FIG. 1B illustrates a tooth repositioning system 101 including a plurality of appliances 103A, 103B, 103C. Any of the appliances described herein can be designed and/or provided as part of a set of a plurality of appliances used in a tooth repositioning system. Each appliance may be configured so a tooth-receiving cavity has a geometry corresponding to an intermediate or final tooth arrangement intended for the appliance. The patient's teeth can be progressively repositioned from an initial tooth arrangement to a target tooth arrangement by placing a series of incremental position adjustment appliances over the patient's teeth. For example, the tooth repositioning system 101 can include a first appliance 103A corresponding to an initial tooth arrangement, one or more intermediate appliances 103B corresponding to one or more intermediate arrangements, and a final appliance 103C corresponding to a target arrangement. A target tooth arrangement can be a planned final tooth arrangement selected for the patient's teeth at the end of all planned orthodontic treatment. Alternatively, a target arrangement can be one of some intermediate arrangements for the patient's teeth during the course of orthodontic treatment, which may include various different treatment scenarios, including, but not limited to, instances where surgery is recommended, where interproximal reduction (IPR) is appropriate, where a progress check is scheduled, where anchor placement is best, where palatal expansion is desirable, where restorative dentistry is involved (e.g., inlays, onlays, crowns, bridges, implants, veneers, and the like), etc. As such, it is understood that a target tooth arrangement can be any planned resulting arrangement for the patient's teeth that follows one or more incremental repositioning stages. Likewise, an initial tooth arrangement can be any initial arrangement for the patient's teeth that is followed by one or more incremental repositioning stages.

Optionally, in cases involving more complex movements or treatment plans, it may be beneficial to utilize auxiliary components (e.g., features, accessories, structures, devices, components, and the like) in conjunction with an orthodontic appliance. Examples of such accessories include but are not limited to elastics, wires, springs, bars, arch expanders, palatal expanders, twin blocks, occlusal blocks, bite ramps, mandibular advancement splints, bite plates, pontics, hooks, brackets, headgear tubes, springs, bumper tubes, palatal bars, frameworks, pin-and-tube apparatuses, buccal shields, buccinator bows, wire shields, lingual flanges and pads, lip pads or bumpers, protrusions, divots, and the like. In some embodiments, the appliances, systems and methods described herein include improved orthodontic appliances with integrally formed features that are shaped to couple to such auxiliary components, or that replace such auxiliary components.

The presently disclosed methods, systems and apparatus can be used to more accurately determine the force systems to move teeth. Also, the CoR, if available, can be more accurately determined to move each of the teeth. Alternatively or in combination, the lines of resistance in response to a force with an orientation to the tooth can be used to determine the location and orientation of a force vector to provide translation, and also additional forces and counterforces to provide an appropriate tooth movement. This approach can be particularly well suited for moving combinations of teeth in different directions and orientations, in accordance with some embodiments.

Figure 1C:
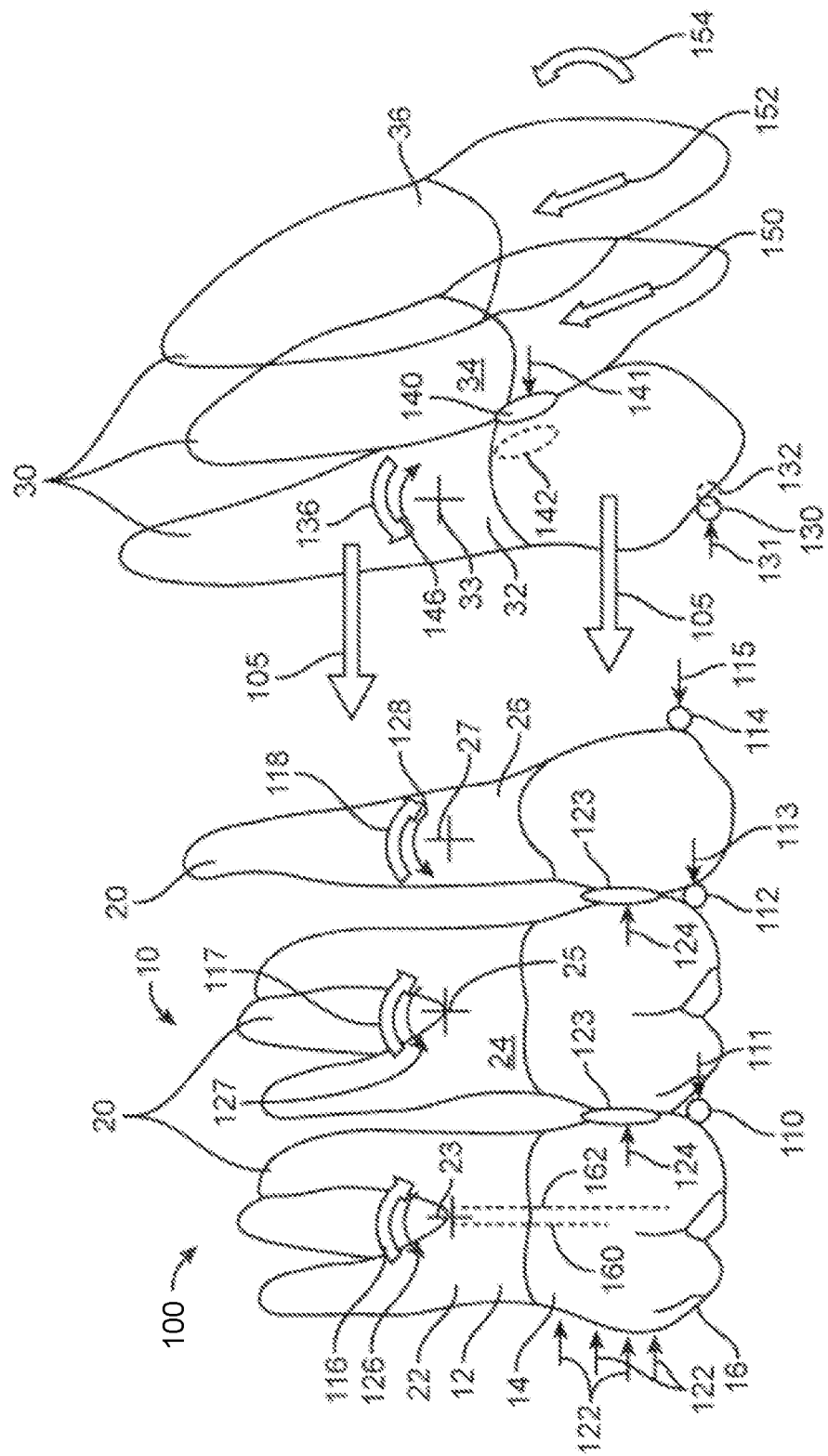
FIG. 1C illustrates a method of orthodontic treatment using a plurality of appliances, in accordance with some embodiments.

FIG. 1C shows a force system of an oral appliance 100. Each of the plurality of teeth may correspond to a 3D model of each of the plurality of teeth at a stage of treatment, and each of the plurality of forces may comprise a 3D force vector and each of the plurality of moments may comprise a 3D moment. The oral appliance 100 may comprise one or more of the polymeric shell appliances configured and arranged to provide teeth moving forces as described herein. Each tooth of the plurality of teeth 10 comprises a root 12 and a crown 14, and the polymeric appliance can apply forces to the crown on the crown in order to move each tooth. The forces applied in this way may be combined with, or applied in alternative to, or in addition to, the forces that may be applied by the action of a polymeric shell on tooth attachments. Each tooth of the plurality of teeth can move with respect to a CoR.

The plurality of teeth 10 may comprise two or more of any teeth of the mouth. The plurality of teeth 10 may comprise one or more of a plurality of posterior teeth 20 such as a plurality of molars or bicuspids and combinations thereof. The plurality of posterior teeth 20 may comprise one or more of a bicuspid 26, a first molar 24 or a second molar 22, for example. The plurality of posterior teeth may comprise a third molar comprising a wisdom tooth, for example. Alternatively or in combination, the plurality of teeth 10 may comprise one or more of a plurality of anterior teeth 30. The plurality of anterior teeth may comprise one or more of a bicuspid, a cuspid (canine), or incisor, for example. In some embodiments, the plurality of anterior teeth 30 comprises a cuspid 32, (canine) and one or more adjacent incisors, such as incisor 34 and incisor 36.

Many embodiments as disclosed herein are particularly well suited for closing extraction sites, such as an extraction site between the posterior teeth 20 and the anterior teeth 30. In some embodiments one or more teeth are moved to fill an extraction site with a movement in a target direction 105. Although the target direction 105 can extend in any direction, in some embodiments the target direction 105 extends along a sagittal direction (e.g., along a mesial-distal direction). The amount of tipping and/or counter rotation can be controlled with the size and shape of the appliance, engagement structures of the appliance, in order to direct movement of the tooth with appropriate amounts of force.

In some embodiments, each tooth comprises a CoR to forces applied to the tooth, and the tooth may rotate about the CoR, or approximately rotate in three dimensions about the CoR. The CoR can be determined computationally, for example with modeling such as finite element modeling as described herein. In some embodiments, the CoR comprises a location on the tooth through which a force from any direction will result in only translation of the tooth, e.g. without rotation. In some embodiments, the location of on the tooth that results in only translation changes with an orientation of the displacement vector. In such embodiments, the orientation of the desired tooth displacement is determined, and the location on the tooth that results in only translation with the force applied to the location is used to determine the forces and moments to the tooth to determine the desired rotational and translational movements, similarly to the CoR, as described herein.

The first molar 24 may comprise a CoR 25 located near the trifurcation of the roots. The second molar 22 may comprise a CoR 23 located near the trifurcation of the roots. The bicuspid 26 may comprise a CoR 27, for example. The cuspid 32 may comprise a CoR 33. Each of the incisor 34 and the incisor 36 may comprise a CoR. The location of each of the centers of resistance of the plurality of teeth as described herein may correspond to a CoR known to a person of ordinary skill the art.

The application of force to a tooth in order to move the tooth can result in a moment to the tooth about the CoR. In some embodiments, a target tooth to be moved such as cuspid 32 receives a force from the polymeric shell appliance, which can be a direct force from the surface of the interior of the shell or indirect through an attachment and combinations thereof. Direct fabrication of the polymeric shell allows the formation of an interproximal tooth engagement structure on the shell, such that when worn, the engagement structure contacts the tooth at an interproximal engagement location 140. Depending on the size of interproximal gap, such as that between teeth 32 and 34, the interproximal tooth engagement structure may extend through the interproximal region, or it may comprise more than one structure, located in similar positions on the lingual and buccal sides of the interproximal gap, respectively.

In some embodiments, a posterior-most tooth comprises a substantial exposed surface 16 suitable for engagement with the polymeric appliance. The polymeric shell appliance 11 can generate force along the posterior surface of the crown at a locus of engagement as indicated with arrows 122. Alternatively or additionally, interproximal tooth engagement structures may be fabricated to engage teeth at one or more interproximal locations 123 to provide interproximal forces indicated with arrows 124. The anteriorly directed force indicated with arrows 122 and/or arrows 124 generates a moment 126 about the CoR 23 of second molar 22, for example. In some embodiments, the force of the appliance indicated with arrows 122 and/or arrows 124 generates a moment 127 around the CoR 25 of first molar 24, and a moment 128 about the CoR 27 of the bicuspid 26, for example. One or more of the plurality of posterior teeth may contact engagement structures at locations such as 110, 112, or 114 to generate a counter moment. Alternatively, structures to cause these counter moments may be omitted, due to the relatively smaller effect of moments 126, 127, and 128.

The contact between a tooth engagement structure and the tooth at location 110 can generate a counter force as indicated with arrow 111 opposite the force indicated with arrows 122 in order to generate a counter moment 116. The counter moment 116 can be greater than moment 126, such that the crown of second molar 22 is rotated away from first molar 24, for example with the differential moment resulting from the sum of moment 126 with counter moment 116. Alternatively, counter moment 116 can be less than moment 126 and also inhibit rotation of second molar 22 toward first molar 24. The moment and counter moment of each tooth can be determined based on the amount of force applied to the tooth and the distance from the CoR to the location of the force along the elongate axis of the tooth. The force shown with arrows 122 is applied at distance 160 along the elongate axis of the tooth from the CoR 23. The counter force shown with arrow 111 is applied at a distance 162 from the CoR 23. In some embodiments, the moment 126 approximately equals the product of the distance 160 and the force represented by arrows 122. The counter moment at location 112 approximately equals the product of distance 162 and the counter force on location 110 represented by arrow 111. A person of ordinary skill in the art will recognize may ways to determine the moments as described herein, for example with finite element modeling and integrating the moments at a plurality of positions relative to the CoR along the tooth.

The contact between a tooth engagement structure and the tooth at location 112 can generate a counter force as indicated with arrow 113 opposite the force indicated with arrows 122 in order to generate a counter moment 117. The counter moment 117 can be greater than moment 127, such that the crown of first molar 24 is rotated away from bicuspid 26, for example with the differential moment resulting from the sum of moment 127 with counter moment 117. Alternatively, counter moment 117 can be less than moment 127 and also inhibit rotation of first molar 24 toward bicuspid 26.

The contact between a tooth engagement structure and the tooth at location 114 can generate a counter force as indicated with arrow 115 opposite the force indicated with arrows 122 in order to generate a counter moment 118. The counter moment 118 can be greater than moment 128, such that the crown of bicuspid 26 is rotated away from the target tooth comprising cuspid 32, for example with the differential moment resulting from the sum of moment 128 with counter moment 118. Alternatively, counter moment 118 can be less than moment 128 and also inhibit rotation of bicuspid 26 toward the target tooth comprising cuspid 32.

In some embodiments, movement of one or more teeth along a target vector can result in movement of one or more adjacent teeth. In some embodiments, movement of cuspid 32 toward the extraction site can result in extrusion of one or more adjacent incisors, for example incisor 34 and incisor 36. In some embodiments, polymeric shell appliance 11 is configured to provide one or more activation forces to one or more teeth. The polymeric shell appliance 11 can be configured with activation of the polymeric shell to apply an activation force 150 to incisor 34. In some embodiments, the activation force 150 is not sufficient to intrude incisor 34 with incisor 34 in the target position, and activation force 150 is sufficient to inhibit extrusion of incisor 34. Extrusion of incisor 34 with movement of cuspid 32 can result in an increased deflection of appliance 11 and increased activation force 150 in order to inhibit further extrusion of incisor 34. Similarly, the polymeric shell appliance can apply an activation force 152 and moment 154 to incisor 36 to inhibit extrusion and tipping of incisor 36.

Figure 2:
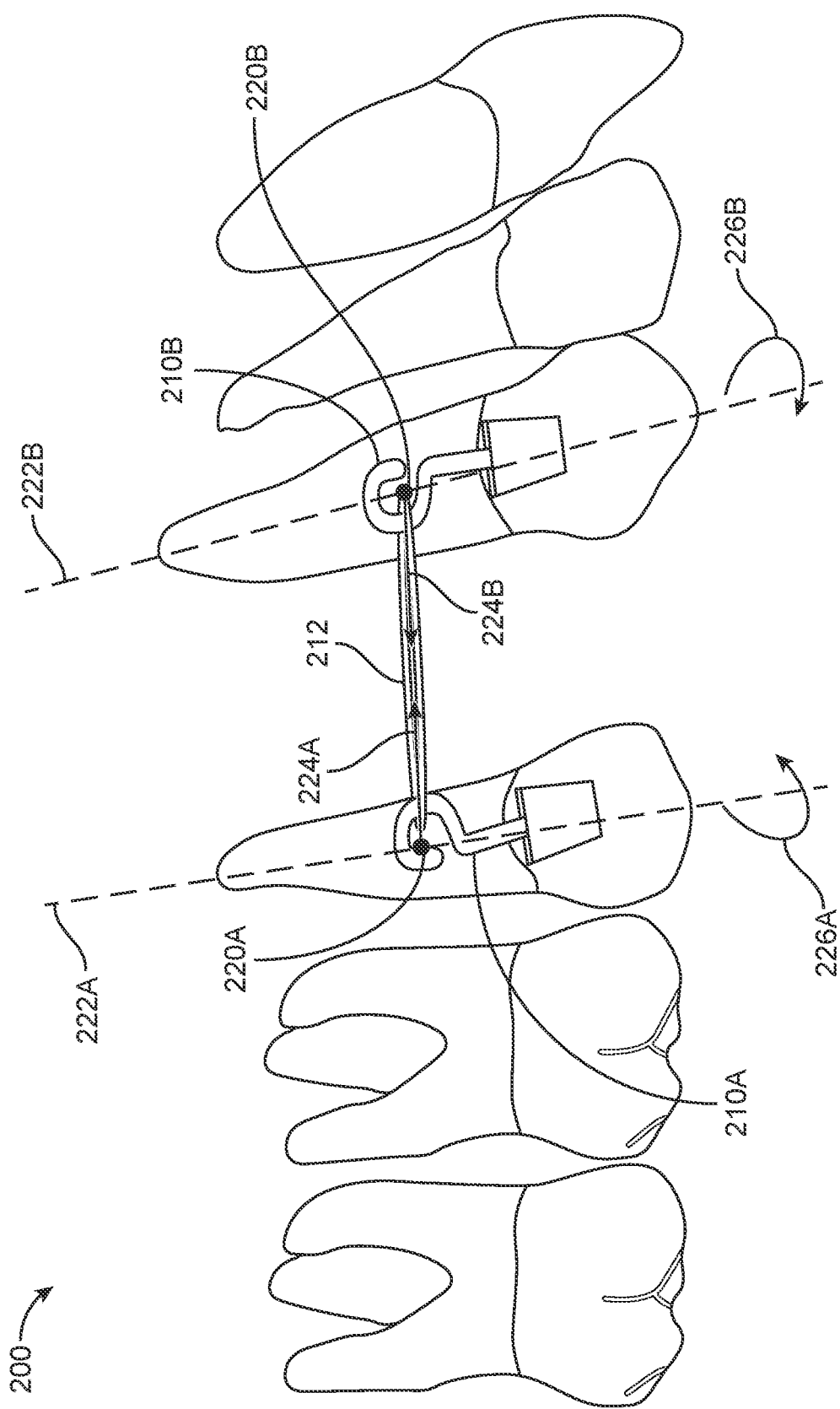
FIG. 2 illustrates an oral appliance system that includes power arms, in accordance with some embodiments.

FIG. 2 illustrates an oral appliance system 200 that may include a first power arms 210A and a second power arm 210B. Power arms 210, 210B may be directly anchored to two nearby teeth, as shown in FIG. 2. Power arms 210A, 210B may be made of a material with stiffness to add rigidity, such as metal, polymer, etc., and may include hook portions for receiving a band 212 stretched between the hook portions. Band 212 may be made of a resistive material, such as rubber, that tends to resist stretching such that band 212 may apply forces, e.g., forces 224A, 224B, to power arms 210A, 210B. Power arms 210A, 210B may be configured such that forces 224A, 224B may reposition the corresponding teeth.

To achieve a desired tooth movement, forces 224A, 224B may be applied to centers of resistances 220A, 220B of the respective teeth, and resultant moments 226A, 226B may be applied with respect to elongate axes of the respective teeth. Although reference is made to centers of resistance, in some embodiments these locations correspond to locations on the tooth through which an applied force results in only displacement, although the location of the CoR may vary, depending on the orientation of the applied force. In embodiments where the centers of resistances 220A, 220B can be determined, power arms 210A-B may be configured to apply forces 224A, 224B and moments 226A, 226B in order to predictably move the corresponding teeth. Alternatively or in combination, the appliance can be configured to apply counter forces and moments if appropriate. For example, appliance 100 can be configured to apply a counter moment to moment 226A if no rotation of the tooth is desired, e.g. no rotation about axis 222A. As seen in FIG. 2, power arms 210A-B may be configured such that forces 224A, 224B generated by band 212 may align with centers of resistance 220A, 220B and/or elongate axes of tooth 222A, 222B. Power arms 210A, 210B may further be configured such that moments 226A, 226B may be applied to generate desired tooth movement. Alternatively or in combination, the appliance 100 can be configured to apply moments in opposite directions in order to decrease rotation of the teeth about axes 222A, 222B, respectively.

Figure 3:
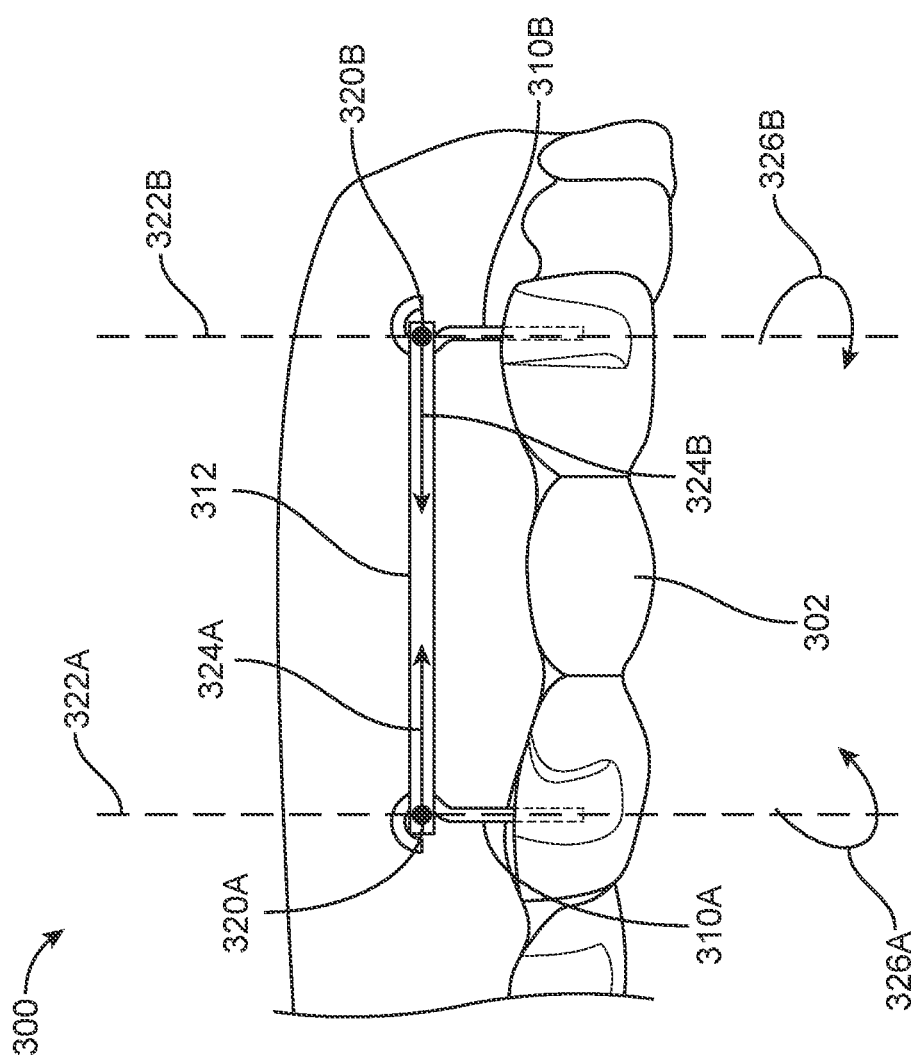
FIG. 3 illustrates an oral appliance system comprising an appliance and power arms placed on teeth, in accordance with some embodiments.

FIG. 3 illustrates an oral appliance system 300 comprising an oral appliance and power arms. Similar to oral appliance system 200, oral appliance system 300 may include power arms 310A, 310B, connected by band 312, in order to apply forces 324A, 324B to centers of resistance 320A, 320B and moments 326A, 326B with respect to elongate axes of tooth 322A, 322B, respectively, to predictably move the corresponding teeth. As seen in FIG. 3, power arms 310A, 310B may be used in conjunction with or other be integrated with an appliance 302.

As illustrated in FIGS. 2 and 3, movement configurations for orthodontic devices, including aligners, power arms, and other oral appliances, may rely on a location of CoR along with other factors. However, due to mechanical and biomechanical factors, such as tooth, periodontal ligament (PDL), and bone geometries and physical properties, in some embodiments a CoR may not exist for some teeth, e.g., when modeled in 3D. As will be discussed further below, when a CoR does not exist mathematically or is unfeasible to calculate, the systems and methods described herein may use the lines of resistance to determine the appropriate configuration of 3D forces and moments to generate a desired movement of a tooth in 3D for a stage of treatment. The principles of structural mechanics and mathematics as described herein may be applied to any geometrical bodies with discreet or continuous surrounding constraints. In some embodiments, the 3D modeling comprising modeling of the tooth, PDL, and bone, for each tooth of a plurality of teeth.

Figure 4A:
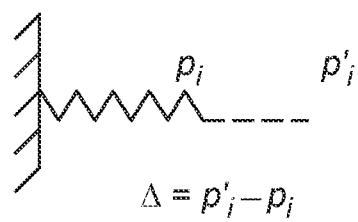
FIG. 4A illustrates a mathematical model representing tooth movement as a one-dimensional (1D) model, in accordance with some embodiments.

FIG. 4A illustrates a mathematical model 400 representing tooth movement as a one-dimensional (1D) model. For a given point $p_i$, the movement ($\Delta$) may be determined from the force applied and the resistance to movement modeled as a spring. The movement $\Delta = p'_i - p_i$, where $p_i$ is the initial tooth position and $p'_i$ is the final tooth position after force has been applied, e.g. for a specific stage of treatment.

Figure 4B:
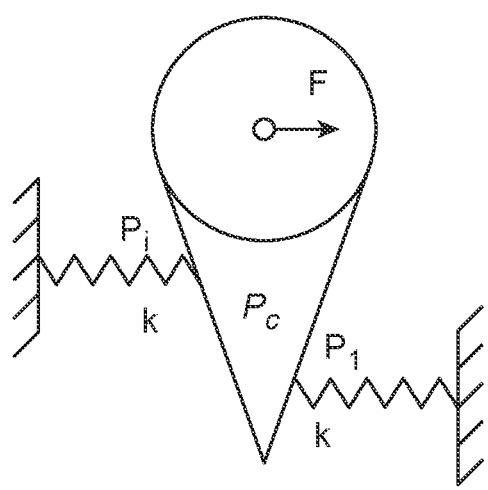
FIG. 4B shows the root of the tooth placed within a recess defined in a rigid surrounding environment, in which the tooth is coupled to the rigid surrounding environment with a plurality of springs, in accordance with some embodiments.

FIG. 4B shows a model 401 of the root of the tooth placed within a recess defined in a rigid surrounding environment, in which the tooth is coupled to the rigid surrounding environment with a plurality of springs. This arrangement corresponds to the tooth positioned in the alveolus of the jaw, in which the tooth is surrounded by the bone of the jaw and coupled to the bone with ligaments, such as the PDL, and other tissue. In some embodiments, the biomechanics of the tooth movement may be modeled as a discreet set of springs coupled to the tooth, in which the springs are coupled to a constraining a rigid body, e.g. alveolar bone, in mathematical model 401. This arrangement can be modeled with a plurality of springs, e.g. $k_1 \ldots k_i$ at appropriate positions. In FIG. 4B, the tooth movement may be modeled by averaging the 1D movement for all points $P_1$ to $P_N$ along the tooth, for example.

In some embodiments, a center point $$P_c = \frac{1}{N}\sum_{i=1}^{N} p_i$$

and we define $P_c$ as an origin (e.g., $P_c=0$), and the tooth is a rigid body. When a force F is applied to the tooth, the tooth may undergo a rotation R (with a moment M) around an axis passing through $P_c$, and a translation T, then $x \rightarrow Rx+T$. With a spring force $G_i = -k(p'_i - p_i)$, the force F may relate by $F + \sum_{i=1}^{N} G_i = 0$ and when substituting T, then $$\frac{1}{kN}F = T.$$

Similarly, the moment M may relate by $M + \sum_{i=1}^{N} G_i \times p'_i = 0$, and when substituting R, then $$\frac{1}{k}M = \sum_{i=1}^{N} Rp_i \times p_i.$$

In some embodiments, the CoR indicates a point where a single force passing through the point produces pure tooth translation T in the direction of the applied force, and at the CoR, moment M=0 and rotation R=I. If we assume $P_c$ is the center of resistance, then $0 = \sum_{i=1}^{N} p_i \times p_i$ for center of resistance $P_c$.

In some embodiments, the spring constants and corresponding stiffnesses are the same, for example with reference to the above equations and the arrangement of FIG. 4B.

In some embodiments the spring constants and corresponding stiffnesses are different (e.g., $k_1$ to $k_N$), then $P_c = \sum_{i=1}^{N} K_i P_i / \sum_{i=1}^{N} K_i$.

Although reference is made to modeling the tooth movement with discrete springs, in some embodiments, the tooth movement can be modeled as an integral over a continuous surface. In such embodiments, the center of resistance $P_c$ may be defined as:

$$P_c = \frac{\iint_S \bar{x} dS}{S} \qquad \text{Equation 1}$$

One of ordinary skill in the art will recognize that a sufficient number of nodes in a discrete model will provide results similar to the continuous equation.

FIG. 5A shows a mathematical model 500 for modeling a tooth as a two-dimensional (2D) model, incorporating aspects from the 1D model described above. Surface 510 may represent a tooth root's surface. Contact nodes 520 may represent contact points between tissue such as the PDL and the tooth, for modeling forces between the PDL and the tooth. PDL nodes 530 may represent internal PDL nodes resisting movement, which are coupled to the tooth on one side and the alveolar bone of the jaw on the other side. For a specific stage of treatment, the coupling to the alveolar bone may comprise a fixed boundary condition. In some embodiments, for subsequent stages of treatment, the boundary condition and position of the alveolar bone can be adjusted in accordance with bone resorption and deposition rates for the amount of force to the tooth.

For a given displacement node ($\delta_1$) at a stage of treatment, there may be a relationship between force vector ($F_1$) and displacement vector ($\Delta_1$). In some embodiments, the displacement node ($\delta_1$) comprises displacement vector, such as a two-dimensional displacement vector, with corresponding components in the X and Y directions. In some embodiments, this displacement node ($\delta_1$) corresponds to a desired tooth movement between two stages of a treatment, for example.

FIG. 5B illustrates a 2D stiffness matrix 501. In some embodiments, the displacement vector $\Delta_1$ comprises a plurality of displacement components, e.g. $\delta_{x1}$, $\delta_{y1}$, and the corresponding force vector ($F_1$) comprises a plurality of force components, $f_{x1}, f_{y1}, f_{x2}, f_{y2} \ldots f_{xi}, f_{yi}$. The relationship among the force, stiffness, and displacement can be expressed with the equation $F_1 = H\Delta_1$, where H is a stiffness matrix for modeling resistance to tooth movement such as PDL resistance. The stiffness matrix H may be based on physiological properties, although other properties may be used, in accordance with the present disclosure. In some embodiments, the elements of the stiffness matrix H correspond to a stiffness of each of the corresponding nodes, such as PDL nodes 530 coupled to tooth boundary nodes 520, for example. The stiffness matrix comprises a plurality of elements corresponding to the plurality of resistance nodes.

With the 2D model the forces and vectors generally lie in a plane, such that the lines of resistance typically converge to a point so as to define the CoR. For example, with the two-dimensional model, there may be two lines of resistance that converge at the CoR.

In accordance with the teachings of the present disclosure, one of ordinary skill in the art of biomechanics can perform mathematical operations to determine appropriate values of the stiffness matrix and equations for determining the lines of resistance and the corresponding intersection at the CoR. Based on the stiffness matrix and orientation of the displacement vector, $f_{x_1} = \sum_{i=1}^{m}\sum_{j=1}^{m} H_{2i-1,2j-1}$, $f_{y_1} = \sum_{i=1}^{m}\sum_{j=1}^{m} H_{2i,2j-1}$, and $M_{z_1} = \sum_{i=1}^{m}\sum_{j=1}^{m}[r_{y_i} \times H_{2i-1,2j-1} + r_{x_i} \times H_{2i,2j-1}]$, and further defining $f_{x_2} = \sum_{i=1}^{m}\sum_{j=1}^{m} H_{2i-1,2j}$, $f_{y_2} = \sum_{i=1}^{m}\sum_{j=1}^{m} H_{2i,2j}$, and $M_{z_2} = \sum_{i=1}^{m}\sum_{j=1}^{m}[r_{y_i} \times H_{2i-1,2j} + r_{x_i} \times H_{2i,2j}]$. In accordance with these equations, the two lines of resistance may be defined as:

$$Y_1 = \frac{f_{y_1}}{f_{x_1}}\left(X_1 - \frac{f_{y_1} M_{z_1}}{f_{y_1}^2 + f_{x_1}^2}\right) - \frac{f_{x_1} M_{z_1}}{f_{y_1}^2 + f_{x_1}^2} \quad \text{Equation 2}$$

$$Y_2 = \frac{f_{y_2}}{f_{x_2}}\left(X_2 - \frac{f_{y_2} M_{z_2}}{f_{y_2}^2 + f_{x_2}^2}\right) - \frac{f_{x_2} M_{z_2}}{f_{y_2}^2 + f_{x_2}^2} \quad \text{Equation 3}$$

In some embodiments, the intersection between the two lines of resistance defines the CoR.

Figure 5C:
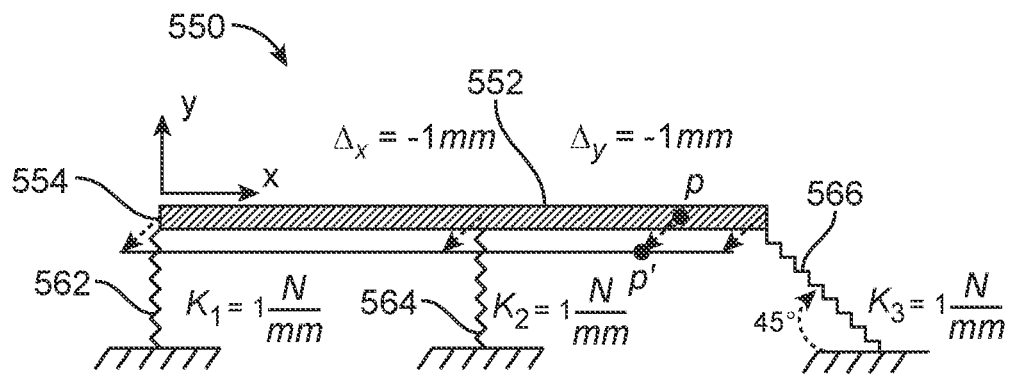
FIGS. 5C and 5D show a force system comprising a movable member coupled to a fixed reference frame with a plurality of springs, in accordance with some embodiments.

FIG. 5C shows force system 550 comprising a movable member 552 coupled to a fixed reference frame 554 with a plurality of springs comprising a first spring 562, a second spring 564 and a third spring 566. This system is helpful for understanding the forces and stiffness matrix components as described herein. This system shows the moveable member subjected to a displacement from p to p' with a corresponding x and y values of $\Delta_x = -1$ mm and $\Delta_y = -1$ mm. The first spring 562 comprises a spring constant $K_1$ of 1 N/mm. The second spring 564 comprises a spring constant $K_2$ of 1 N/mm. The third spring 566 comprises a spring constant $K_3$ of 1 N/mm. The third spring 566 is inclined at an angle such as an angle of 45 degrees with respect to the X and Y axes. Although reference is made to spring constants, the springs may correspond to non-linear values and the value of the spring constant may comprise a coefficient that varies in accordance with the force.

Figure 5D:
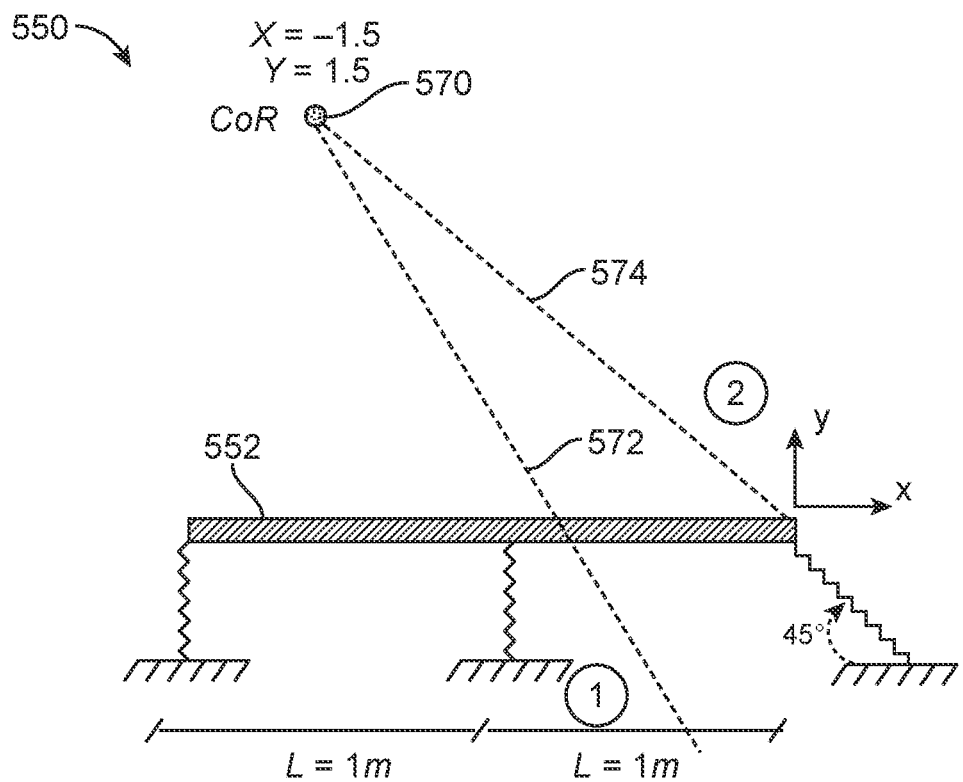

FIG. 5D shows the lines of resistance and corresponding CoR 570 for the force system in FIG. 5C. The lines of resistance comprise a first line of resistance 572 and a second line of resistance 574. The first line of resistance 572 and the second line of resistance 574 intersect at the CoR 570.

The CoR values can be determined by substituting the appropriate values into the above equations to yield the CoR 570 as shown.

With the 2D model, the forces are generally constrained in a plane, such that the determined lines of resistance will typically converge to a point that defines the CoR, in accordance with some embodiments.

With the 3D model of tooth movement, additional conditions can exist that are not present in the 2D model, and these conditions can be used to plan the desired amount of tooth movement and corresponding forces for a specific stage of treatment. In some instances, a first condition exists in which only translation of the tooth in a specific 3D direction can be achieved only by using two forces at two separate locations on the tooth, and in this first condition the lines of resistance effectively do not exist. Alternatively, a second condition may exist in which the lines of resistance exist, but the tooth may or may not have a center of resistance. With this second condition, the lines of resistance can be analyzed to determine whether the lines of resistance substantially intersect, and if the lines of resistance substantially intersect the center of resistance exists and if the lines of resistance do not substantially intersect then the center of resistance does not exist.

With the 3D model of tooth movement, the determined lines of resistance comprise 3D vectors that are not constrained to a plane, and these 3D vectors do not necessarily converge to a point. In some embodiments, modeling can be performed to determine if 3D lines of resistance converge to a point, e.g. to a CoR, or if the 3D lines of resistance do not converge to a point. In embodiments where the 3D lines of resistance do not converge to a point in 3D space, the location of the tooth at which an applied force will result in pure translation changes, depending on the orientation of the displacement applied to the tooth. Therefore for a displacement of a tooth along a 3D displacement vector, it can be helpful to determine the location of the tooth that will provide pure translation, if available, and use this location to determine the appropriate orientation and position of the force vector to the tooth to provide the desired translation and rotation to the tooth as 3D vectors. Also, the shape of the 3D tooth receiving cavity can be defined so as to provide the desired rotation and translation of the tooth in accordance with the determined location of the tooth that provides only translation for the desired tooth displacement.

FIG. 6A shows a mathematical model 600 for modeling a tooth as a three-dimensional (3D) model, as an extension from the 1D and 2D models described above. The variables and equations can be readily extended to 3D in accordance with the teachings of the present disclosure. In some embodiments, the lines of resistance can vary in response to the angles of the force vector and/or displacement vector applied to the tooth, such that the CoR does not remain fixed. The presently disclosed methods and apparatus are well suited for addressing variations in the CoR with the angle of the applied displacement.

Surface 610 may represent a tooth root's surface. The surface 610 of the tooth of the root may comprise any suitable surface that represents the root. In some embodiments, the surface 610 comprises a conic shape, which can decrease the complexity of the treatment modeling and computations. For example, finite element modeling can be performed on the tooth with a suitably shaped conic root, which is combined with scan data, for example from an intraoral scanner, so as to provide a tooth suitable for finite element modeling. The dimensions of the conic root shape may comprise suitable dimension for a specific tooth, which may be obtained from publications by one of ordinary skill in the art. Alternatively, the surface 610 of the root may comprise data obtained from imaging such as CBCT scanning of the dentition, and this may be combined with other data, such as an intra oral scanner to model the shape of the tooth, for example.

Contact nodes 620 may represent contact points between the PDL and the tooth, for modeling a reaction from the PDL to the tooth. While the modeling can be performed in many ways, in some embodiments the modeling comprises finite element modeling. The surface of the root of the tooth may comprises a simplified, model of the root of the tooth, such as a conic surface or an elliptical surface modeling the surface of the tooth. Work in relation to the present disclosure suggests that the simplified surface in combination with the lines of resistance can be sufficient to provide improve modeling of the tooth resistance. Alternatively or in combination, the surface of the tooth may comprise surface of the root imaged as described herein, such as with cone beam computed tomography (CBCT). The PDL nodes 630 may represent internal PDL nodes resisting movement. In some embodiments, the PDL nodes are configured to correspond to a thickness of the PDL between the tooth and the PDL node, and this thickness may comprise any suitable thickness, for example within a range from about 0.5 mm to about 3 mm. Although finite element modeling may be used to determine the lines of resistance at each of a plurality of stages, this approach can be computationally more efficient than providing a more detailed finite element analysis such as transient finite element modeling of the tooth movement at each of the plurality of stages.

For a given displacement ($\delta_1$) at a stage of treatment of the tooth, there may be a relationship between forces ($F_1$) and displacements ($\Delta_1$). The displacement vector 61 comprises plurality components $\delta_x$, $\delta_y$, and $\delta_z$ along the x, y and z axes, respectively. The relationship between forces ($F_1$) and displacements ($\Delta_1$) can generally be expressed as $F_1 = H\Delta_1$, where H is a stiffness matrix for three-dimensional modeling of resistance, such as PDL resistance. The corresponding force components $f_{x1}$, $f_{y1}$, $f_{z1}$ . . . $f_{xi}$, $f_{yi}$, $f_{zi}$, can be determined based on the stiffness matrix and displacement vector. Although reference is made to biomechanical properties, these may or may not be based on properties of a particular patient. Work in relation to the present disclosure suggests that biomechanical properties based on ranges of populations can be used to determine the lines of resistance, and the data for the ranges can be combined with demographic information of the patient, such as one or more of age or gender. FIG. 6B illustrates a stiffness matrix 601 for the 3D model. In the 3D model, there may be up to three lines of resistance. In some embodiments, the 3D model comprises an extension of the 2D model as described herein, and includes additional elements such as $f_z$, $M_x$, and $M_y$, for example.

$$M \cdot F = M_x f_x + M_y f_y + M_z f_z \qquad \text{Equation 4}$$

Equation 4 may be used to determine whether a CoR exists for the 3D model of a tooth, and if the CoR exists the location of the CoR can be determined as described herein. If the CoR does not exist, forces can be determined to move the tooth.

In a first condition $M \cdot F \neq 0$. In this first condition a CoR does not exist. In this condition two translational forces in a specific orientation at two locations can be applied to the tooth to move the tooth with only translation, and an appliance can be configured to generate the two generate the two translational forces at the two locations on the tooth with the appropriate orientation. In some embodiments, in this first condition the lines of resistance do not exist and two forces are required to make a desired translation.

In a second condition $M \cdot F = 0$. For the second condition, the lines of resistance exist, but a CoR may or may not exist. The lines of resistance can be used to determine if CoR exists. If the lines of resistance substantially intersect, then the CoR exists. In this second condition, the lines of resistance can be determined for forces in a plurality of directions, such as along the x, y and z axes, respectively. The lines of resistance can be used to determine if the CoR exists (e.g., a point where the three lines of resistance intersect). The lines of resistance can be determined by substituting appropriate values for $\delta_x$, $\delta_y$, and $\delta_z$, for example: $\delta_x = 1$, and $\delta_y = \delta_z = 0$ for the first line of resistance; $\delta_x = 0$, $\delta_y = 1$, and $\delta_z = 0$ for the second line of resistance; and $\delta_x = 0$, $\delta_y = 0$, and $\delta_z = 1$ for the third line of resistance. For example, the lines of resistance can be calculated by substituting appropriate values of $\delta_x$, $\delta_y$, and $\delta_z$, in which $$R_x = -\left(\frac{M_y(f_y^2 + f_z^2) + M_x(f_x f_y)}{f_z(f_x^2 + f_y^2 + f_z^2)}\right),$$

$$R_y = -\left(\frac{M_z(f_x^2 + f_z^2) + M_y(f_y f_z)}{f_x(f_x^2 + f_y^2 + f_z^2)}\right), \text{ and}$$

$$R_z = -\left(\frac{M_x(f_x^2 + f_y^2) + M_z(f_x f_z)}{f_y(f_x^2 + f_y^2 + f_z^2)}\right),$$

in which the lines of resistance may be calculated by:

$$\frac{x - R_x}{f_x} = \frac{y - R_y}{f_y} = \frac{z - R_z}{f_z} \qquad \text{Equation 5}$$

In some embodiments, if the lines of resistance do not intersect sufficiently close at a single point, the CoR does not exist. In such embodiments, it can be helpful to determine the location of the tooth that provides only translation for the displacement vector in the specific orientation. This location of the tooth can be used to determine the location and orientations of the forces to the tooth to provide the desired translational and rotational movement of the tooth at the stage of treatment.

Figure 7:
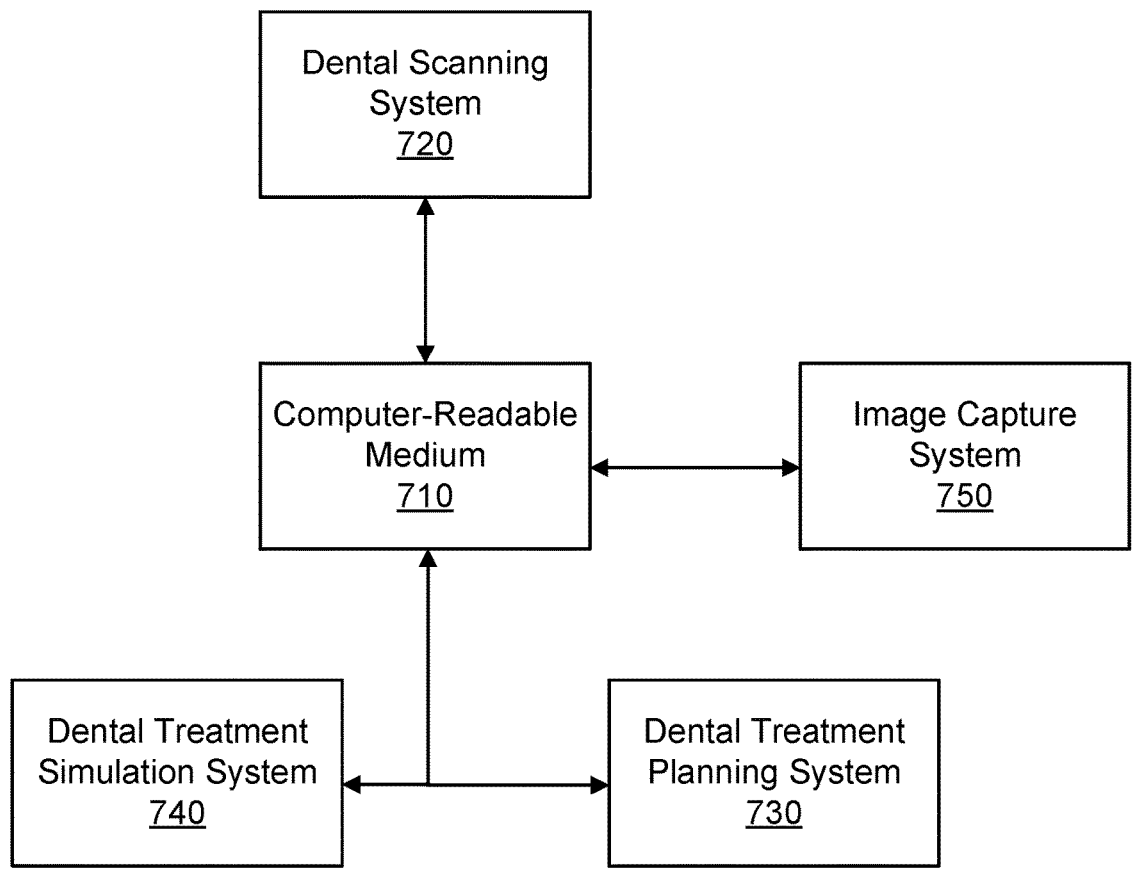
FIG. 7 shows a system for simulating and planning an orthodontic treatment, in accordance with some embodiments.

FIG. 7 shows a system 700 for simulating and planning an orthodontic treatment, in accordance with some embodiments. In the example of FIG. 7, the system 700 includes a computer-readable medium 710, a dental scanning system 720, a dental treatment planning system 730, a dental treatment simulation system 740, and an image capture system 750. One or more of the elements of the system 700 may include elements of such as those described with reference to the computer system shown in FIG. 8 and vice versa. One or more elements of system 700 may also include one or more computer readable media including instructions that when executed by a processor, for example, a processor of any of systems 720, 730, 740, and 750 cause the respective system or systems to perform the processes described herein.

Dental scanning system 720 may include a computer system configured to capture one or more scans of a patient's dentition. Dental scanning system 720 may include a scan engine for capturing 2D or 3D images of a patient. Such images may include images of the patient's teeth, face, and jaw, for example. The images may also include x-rays, computed tomography, magnetic resonance imaging (MRI), cone beam computed tomography (CBCT), cephalogram images, panoramic x-ray images, digital imaging and communication in medicine (DICOM) images, or other subsurface images of the patient. The scan engine may also capture 3D data representing the patient's teeth, face, gingiva, or other aspects of the patient.

Dental scanning system 720 may also include a 2D imaging system, such as a still or video camera, an x-ray machine, or other 2D imager. In some embodiments, dental scanning system 720 may also include a 3D imager, such as an intraoral scanner, an impression scanner, a tomography system, a cone beam computed tomography (CBCT) system, or other system as described herein, for example. Dental scanning system 720 and associated engines and imagers can be used to capture the historic scan data for use in determining the historic mean parameters of a 3D parametric dental model, as described herein. Dental scanning system 720 and associated engines and imagers can be used to capture the 2D and 3D images of a patient's face and dentition for use in building a 3D parametric model of the patient's teeth as described herein. Examples of parametric models of the patient's teeth suitable for incorporation in accordance with the present disclosure are describe in U.S. application Ser. No. 16/400,980, filed on May 1, 2019, entitled "Providing a simulated outcome of dental treatment on a patient", published as US20200000551 on Jan. 2, 2020, the entire disclosure of which is incorporated herein by reference.

Dental treatment simulation system 740 may include a computer system configured to simulate one or more estimated and/or intended outcomes of a dental treatment plan. In some implementations, dental treatment simulation system 740 obtains photos and/or other 2D images of a consumer/patient. Dental treatment simulation system 740 may further be configured to determine tooth, lip, gingiva, and/or other edges related to teeth in the 2D image. As noted herein, dental treatment simulation system 740 may be configured to match tooth and/or arch parameters to tooth, lip, gingiva, and/or other edges. Dental treatment simulation system 740 may also render a 3D tooth model of the patient's teeth. Dental treatment simulation system 740 may gather information related to historical and/or idealized arches representing an estimated outcome of treatment. Dental treatment simulation system 740 may, in various implementations, insert, align, etc. the 3D tooth model with the 2D image of the patient in order to render a 2D simulation of an estimated outcome of orthodontic treatment. Dental treatment simulation system 740 may include a photo parameterization engine which may further include an edge analysis engine, an EM analysis engine, a course tooth alignment engine, and a 3D parameterization conversion engine. The dental treatment simulation system 740 may also include a parametric treatment prediction engine which may further include a treatment parameterization engine, a scanned tooth normalization engine, and a treatment plan remodeling engine. Dental treatment simulation system 740 and its associated engines may carry out the processes described herein, for example with reference to FIGS. 9-10.

Dental treatment planning system 730 may include a computer system configured to implement treatment plans. Dental treatment planning system 730 may include a rendering engine and interface for visualizing or otherwise displaying the simulated outcome of the dental treatment plan. For example, the rendering engine may render the visualizations of the 3D models described herein. Dental treatment planning system 730 may also determine an orthodontic treatment plan for moving a patient's teeth from an initial position, for example, based in part on the 2D image of the patient's teeth, to a final position. Dental treatment planning system 730 may be operative to provide for image viewing and manipulation such that rendered images may be scrollable, pivotable, zoomable, and interactive. Dental treatment planning system 730 may include graphics rendering hardware, one or more displays, and one or more input devices. Some or all of dental treatment planning system 730 may be implemented on a personal computing device such as a desktop computing device or a handheld device, such as a mobile phone. In some embodiments, at least a portion of dental treatment planning system 730 may be implemented on a scanning system, such as dental scanning system 720. Image capture system 750 may include a device configured to obtain an image, including an image of a patient. The image capture system may comprise any type of mobile device (iOS devices, iPhones, iPads, iPods, etc., Android devices, portable devices, tablets), PCs, cameras (DSLR cameras, film cameras, video cameras, still cameras, etc.). In some implementations, image capture system 750 comprises a set of stored images, such as images stored on a storage device, a network location, a social media website, etc.

Figure 8:
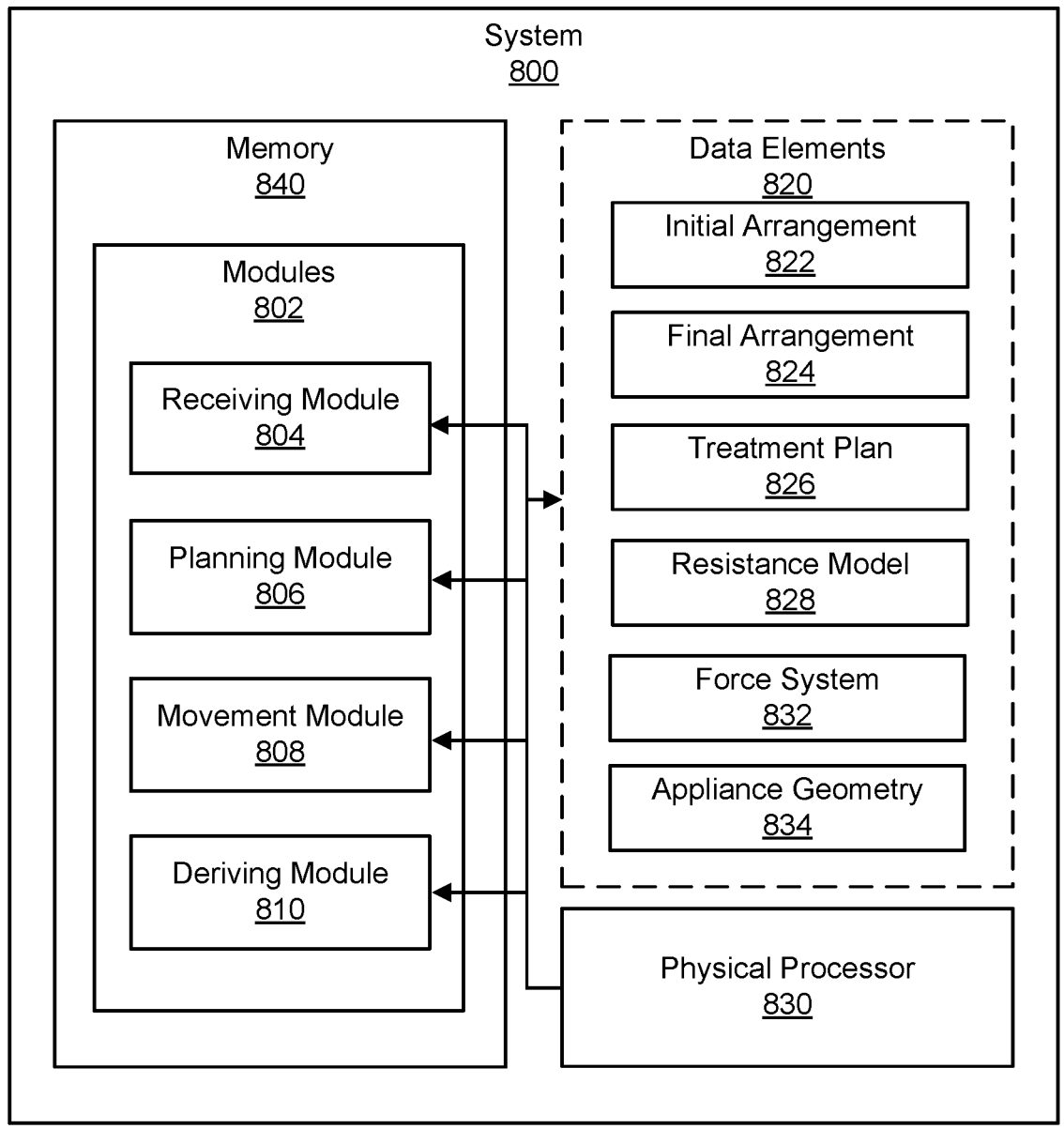
FIG. 8 shows a block diagram of an example system for treatment planning with CoR data, in accordance with some embodiments.

FIG. 8 shows a block diagram of an example system 800 for treatment planning with CoR data. As illustrated in this figure, example system 800 may include one or more modules 802 for performing one or more tasks. As will be explained in greater detail below, modules 802 may include a receiving module 804, a planning module 806, a movement module 808, and a deriving module 810. Although illustrated as separate elements, one or more of modules 802 in FIG. 8 may represent portions of a single module or application.

In some embodiments, one or more of modules 802 in FIG. 8 may represent one or more software applications or programs that, when executed by a computing device, may cause the computing device to perform one or more tasks. For example, and as will be described in greater detail below, one or more of modules 802 may represent modules stored and configured to run on one or more computing devices, such as the devices illustrated in FIGS. 7, 11, and/or 12. One or more of modules 802 in FIG. 8 may also represent all or portions of one or more special-purpose computers configured to perform one or more tasks.

As illustrated in FIG. 8, example system 800 may also include one or more memory devices, such as memory 840. Memory 840 generally represents any type or form of volatile or non-volatile storage device or medium capable of storing data and/or computer-readable instructions. In one example, memory 840 may store, load, and/or maintain one or more of modules 802. Examples of memory 840 include, without limitation, Random Access Memory (RAM), Read Only Memory (ROM), flash memory, Hard Disk Drives (HDDs), Solid-State Drives (SSDs), optical disk drives, caches, variations or combinations of one or more of the same, and/or any other suitable storage memory.

As illustrated in FIG. 8, example system 800 may also include one or more physical processors, such as physical processor 830. Physical processor 830 generally represents any type or form of hardware-implemented processing unit capable of interpreting and/or executing computer-readable instructions. In one example, physical processor 830 may access and/or modify one or more of modules 802 stored in memory 840. Additionally or alternatively, physical processor 830 may execute one or more of modules 802 to facilitate treatment planning. Examples of physical processor 830 include, without limitation, microprocessors, microcontrollers, Central Processing Units (CPUs), Graphics Processing Units (GPUs), logic circuitry, gate arrays, Field-Programmable Gate Arrays (FPGAs) that implement softcore processors, Application-Specific Integrated Circuits (ASICs), portions of one or more of the same, variations or combinations of one or more of the same, and/or any other suitable physical processor.

As illustrated in FIG. 8, example system 800 may also include one or more data elements 820, such as initial arrangement 822, final arrangement 824, treatment plan 826, resistance model 828, force system 832, and appliance geometry 834. Data elements 820 generally represent any type or form of data, such as medical imaging data, treatment planning data, appliance configurations, and permutations thereof, as will be described further below.

The initial arrangement 822 corresponds to an initial arrangement of the plurality of teeth prior to treatment. The initial arrangement 822 can be obtained by receiving digital data from scans of the teeth and may comprise parametric data of the teeth as described herein.

The final arrangement 824 corresponds to the final intended arrangement of the plurality of teeth. The final arrangement 824 may comprise positions and orientations, e.g. the pose, of each of the plurality of teeth upon completion of the treatment. The final arrangement 824 can be determined in many ways. For example, a treatment professional may manipulate the teeth of the patient with software to determine the final intended locations of the plurality of treated teeth. Although reference is made to a final position of each of the teeth, in some embodiments moving the teeth substantially toward the final intended position can be sufficient for the treatment to be successful. In some embodiments, when the patient is able to wear the last appliance of a plurality of appliances, the teeth have moved substantially toward the final intended position.

While the treatment plan 826 can be configured in many ways, in some embodiments the treatment plan 826 comprises a plurality of stages of treatment. The stages may comprise successive stages of treatment, in which each of the one or more repositioned teeth is moved incrementally. For each stage, movements such as displacements of the one or more repositioned teeth can be determined in order to move the teeth with the stage of treatment. Each appliance for a given stage may comprise a plurality of teeth receiving cavities sized and shaped to move the one or more teeth in accordance with the stage of treatment.

While the resistance model 828 can be configured in many ways, in some embodiments, the resistance model determines the axes of resistance for each of a plurality of stages, for example with a stiffness matrix as described herein. The axes of resistance can be used to determine the location of a tooth that provides only translation for a force through the location of the tooth, which corresponds to the center of resistance. In some embodiments, the resistance model determines if the center of resistance exists, and if the center of resistance exists the center of resistance is used in the resistance model. Alternatively or in combination, if the 3D lines of resistance to do substantially intersect, the direction of displacement for the stage of the treatment for the tooth can be used to determine the location of the tooth through which a force vector in the direction of the displacement provides only displacement of the tooth, e.g. without rotation. This position can be used to determine other forces and moments suitable to move the tooth in accordance with the tooth movement for that stage of treatment.

While the force system 832 can be configured in many ways, in some embodiments, the resistance of the tooth to movement from the resistance model can be used to determine a suitable amount of displacement for the tooth at a stage of treatment. For example, a limit on force or a preferred range of forces can be established, so as to determine the amount of force and corresponding displacement of the tooth. The rotation of the tooth about the center of resistance can be similarly determined and can be combined with other forces such as translational forces, in order to determine suitable locations and forces to the tooth to provide the intended displacement and rotation for the stage of treatment.

The treatment plan, resistance model, and force system can be iteratively updated in order to develop the treatment plan. For example, if tooth movement such as one or more of a rotation or a displacement would result in excessive force to the tooth, the amount of displacement can be decreased. Alternatively, if the forces to a tooth are low, the amount of movement such as one or more of a rotation or a translation can be increased so as to move the tooth more at the stage of treatment.

While the appliance geometry 834 can be configured in many ways, in some embodiments the appliance geometry is configured to provide the forces and force couplings to the tooth to provide the desired movement of the tooth. The shape and orientation of the tooth receiving cavity and other appliance parameters can be configured to provide forces to the tooth as the appliance deforms slightly when placed on the teeth.

Figure 9:
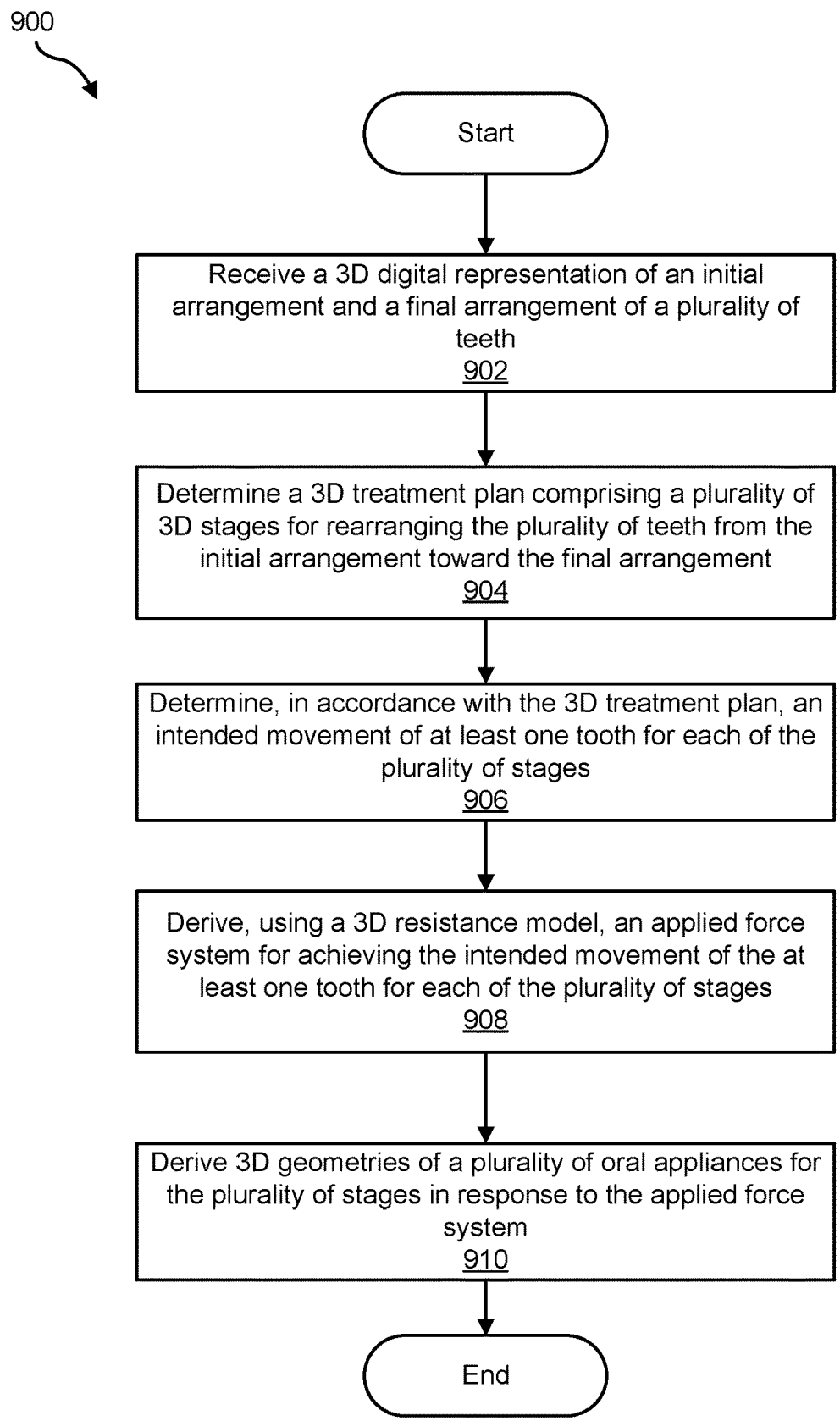
FIG. 9 is a flow diagram of an example computer-implemented method for determining appliance geometries with center of resistance data, in accordance with some embodiments.

FIG. 9 is a flow diagram of an example computer-implemented method 900 for determining appliance geometries with CoR data. The steps shown in FIG. 9 may be performed by any suitable computer-executable code and/or computing system, including system 800 in FIG. 8, and/or any of the systems in FIGS. 7, 11, and/or 12, and/or variations or combinations of one or more of the same. In one example, each of the steps shown in FIG. 9 may represent an algorithm whose structure includes and/or is represented by multiple sub-steps, examples of which will be provided in greater detail below.

As illustrated in FIG. 9, at step 902 one or more of the systems described herein may receive a 3D digital representation of an initial arrangement and a final arrangement of a plurality of teeth. For example, receiving module 804 may receive initial arrangement 822 and final arrangement 824.

The 3D digital representation, which may encompass initial arrangement 822 and final arrangement 824, may include a 3D model of the plurality of teeth. Initial arrangement 822 may comprise 3D data based on scan data of a patient such that acquiring the 3D model may include scanning the plurality of teeth using, for example, dental scanning system 720 described above. The 3D scan data may include one or more of optical scan data or cone beam computed tomography (CBCT) data. Final arrangement 824 may include 3D data of an estimated and/or intended outcome of a dental treatment plan. In some implementations, receiving module 804 may store the 3D digital representation of the initial arrangement (e.g., initial arrangement 822) and the 3D digital representation of the final arrangement (e.g., final arrangement 824) in a database (e.g., a patient database or other datastore) after receiving the 3D digital representation.

As illustrated in FIG. 9, at step 904 one or more of the systems described herein may determine a 3D treatment plan comprising a plurality of 3D stages for rearranging the plurality of teeth from the initial arrangement toward the final arrangement. For example, planning module 806 may determine treatment plan 826 for rearranging the plurality of teeth from initial arrangement 822 toward final arrangement 824. Treatment plan 826 may include a plurality of stages for treatment as described herein. Treatment plan 826 may include a complete and/or partial treatment plan and may include, for example, oral appliance geometries and/or designs, modeling data, and/or any other data relevant to treatment plans.

As illustrated in FIG. 9, at step 906 one or more of the systems described herein may determine, in accordance with the 3D treatment plan, an intended movement of at least one tooth for each of the plurality of stages. For example, movement module 808 may determine, in accordance with treatment plan 826, the intended movement of one or more teeth for each of the stages of treatment plan 826.

At step 908, one or more of the systems described herein may derive, using a 3D resistance model, an applied force system for achieving the intended movement of the at least one tooth for each of the plurality of stages. For example, deriving module 810 may use resistance model 828 to derive force system 832 for achieving the intended movement of the at least one tooth for each of the plurality of stages of treatment plan 826. Resistance model 828 may comprise data relating to modeling the tooth-PDL-bone interaction, such as the stiffness matrices described herein, and may be derived from empirical data, computer analysis, etc. In some examples, resistance model 828 may include a CoR for the at least one tooth, for instance when the CoR may be feasibly calculated. Force system 832 may comprise data relating to desired force application, such as locations for applying force, which may be based on a CoR, estimated CoR, or other alternative to CoR.

In some examples, the 3D resistance model may include one or more of a linear 3D resistance model or a non-linear 3D resistance model. For example, based on the calculations described above, the 3D resistance model may include three lines of resistance of the at least one tooth at each of the plurality of stages, such as the three lines of resistance described above. The three lines of resistance may change in response to forces from different directions at each of the plurality of stages.

In some examples, the applied force system may be configured to apply a substantially translational force to the at least one tooth in response to the three lines of resistance and a moment to the at least one tooth in response to the three lines of resistance for each of the plurality of stages. For example, as described above, when a CoR may not be feasibly calculated, an alternative may include calculating one or more lines of resistance and applying a translational force to achieve a desired tooth movement.

In some examples, the applied force system may include a plurality of force vectors. The plurality of force vectors may include a primary force vector and a resultant force vector to apply forces to the at least one tooth for at least one of the plurality of stages. The force vectors may be determined based on the CoR, or alternative when CoR is not available. In some examples, the plurality of force vectors may include three or more force vectors for each of the plurality of stages.

In some examples, the resultant force vector may include a force from a power arm for application of a force at a location away from a surface of the at least one tooth to provide a moment to the at least one tooth. For example, FIG. 2 illustrates how force 224A may provide moment 226A.

In some examples, the three lines of resistance may be determined with finite element modeling (FEM) at each of the plurality of stages. For example, if an exact CoR may not be feasibly calculated, FEM or other similar analysis may be used to determine the lines of resistance.

In some examples, deriving the applied force system may include additional steps, such as analysis steps and additional calculations. Deriving the applied force system may include determining whether the at least one tooth comprises a 3D CoR. As described above, certain calculations may determine whether a 3D CoR is available. For example, the moment and force dot product as described above, an intersection point of the three lines of resistance as described above, FEA and/or FEM, etc. may be used. If a 3D CoR is available, the 3D CoR may change between stages. In some examples, the at least one tooth may include the 3D CoR and the 3D CoR may change from a first stage of the plurality of stages to a second stage of the plurality of stages. In yet other examples, the at least one tooth may include the 3D CoR for a first plurality of stages and may not include the CoR for a second plurality of stages. In other words, the 3D CoR may change for different stages. In some stages, the 3D CoR may not be available and an alternative may be used as described herein. For example, when the at least one tooth does not comprise the 3D CoR, the 3D resistance model may include three lines of resistance. The three lines of resistance may be determined for the at least one tooth for each of the plurality of stages. For instance, the three lines of resistance may be determined for the at least one tooth for every stage (e.g., as a preliminary and/or final calculation) or for certain stages (e.g., only when available or when necessary if no CoR is available).

In some examples, the applied force system may include a 3D force vector applied to the at least one tooth for each of the plurality of stages. The 3D force vector may change in response to a change in the 3D CoR from the first stage to the second stage. In some examples, a 3D force vector to translate the at least one tooth may be determined at each of the plurality of stages in response to the three axes of resistance of the stage. A 3D moment to the at least one tooth may be determined in response to the three axes of resistance at each of the plurality of stages. The 3D force vector may correspond to a translational force to be applied to the tooth and the 3D moment may correspond to a moment to be applied to the tooth.

In some examples, the method 900 may include calculating the force system in response to the intended movement, and calculating a resistance model representing the at least one tooth for providing the force system on the at least one tooth at each of the plurality of stages. For example, the resistance model may further include a translational force and a moment to be applied to the at least one tooth for each of the plurality of stages. The translational force and moment may be applied via the oral appliances, for example with reference to FIG. 1C. In some embodiments, each of the plurality of oral appliances includes a power arm for applying the translational force and the moment to be applied to the at least one tooth for each of the plurality of stages. As seen in FIGS. 2 and 3, power arms 210A-B and/or power arms 310A-B may be configured to apply forces 224A-B and/or forces 324A-B, respectively (which may correspond to the translational force), as well as apply moments 226A-B and/or moments 324A-B, respectively (which may correspond to the moment). The features of the power arms, such as length, location of anchor and hook points, material, etc. may be configured for applying the desired translational force and/or moment.

In some examples, deriving the applied force system may include applying the treatment plan to the 3D model to simulate rearranging the plurality of teeth from the initial arrangement to the final arrangement. For instance, deriving force system 832 may include applying treatment plan 826 to initial arrangement 822 using resistance model 828 to determine if force system 832 produces final arrangement 824, within a tolerable range (e.g., satisfies an efficacy threshold). Using this feedback, force system 832 may be updated until force system 832 is modeled to produce final arrangement 824 within the tolerable range.

The resistance model may include various parameters that may be used for calculations. The parameters of the resistance model may be determined at each of the plurality of stages with finite element modeling (FEM), or other analysis such as FEA. In some examples, the 3D resistance model may include a parameter selected from the group consisting of a PDL Young's modulus, a PDL thickness, a PDL Poisson's ratio and a Bone Young's modulus. The PDL Young's modulus may be within a range from 0.05 to $10^6$ MPa. The PDL thickness may be within a range from 0.1 mm to 4 mm. The Poisson's ratio may be within a range from −1 to 0.5. The Poisson's ratio may be within a range from 0 to 0.49. The Bone Young's modulus may be at least 2000 MPa. In some examples, resistance model 828 may include the Poisson's ratio within a range from 0 to 0.49. In some examples, resistance model 828 may not include or may leave undefined certain parameters.

Returning to FIG. 9, at step 910 one or more of the systems described herein may derive 3D geometries of a plurality of oral appliances for the plurality of stages in response to the applied force system. For example, deriving module 810 may derive appliance geometry 834 in response to force system 832. Appliance geometry 834 may include 3D geometries for oral appliances corresponding to the 3D stages of treatment plan 826. Appliance geometry 834 may be used for fabricating the oral appliances for each stage of treatment plan 826.

In some examples, after deriving appliance geometry 834, method 900 may include fabricating the plurality of oral appliances using the derived geometries. For instance, fabricating the oral appliance may include converting the derived geometry (e.g., appliance geometry 834) into instructions for fabricating the appliance. In certain examples, fabricating the oral appliance may include using one or more of thermoforming and/or direct fabrication.

Figure 10:
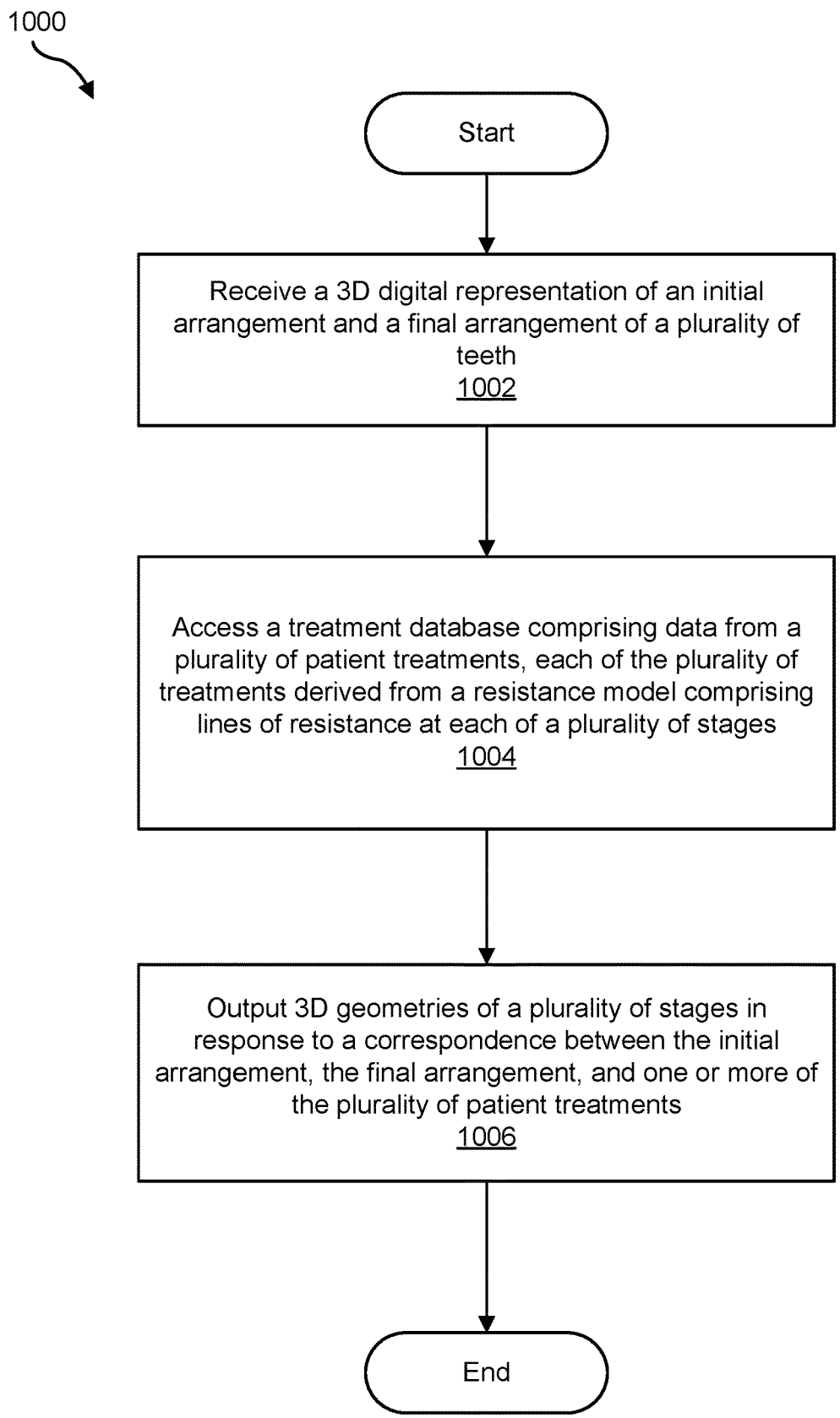
FIG. 10 shows a flow diagram for designing an oral appliance in accordance with a database of treatments comprising data derived from a resistance model, in accordance with some embodiments.

FIG. 10 shows a flow diagram for designing an oral appliance in accordance with a database of treatments comprising data derived from a resistance model. The steps shown in FIG. 10 may be performed by any suitable computer-executable code and/or computing system, including system 800 in FIG. 8, and/or any of the systems in FIGS. 7, 11, and/or 12, and/or variations or combinations of one or more of the same. In one example, each of the steps shown in FIG. 10 may represent an algorithm whose structure includes and/or is represented by multiple sub-steps, examples of which will be provided in greater detail below.

As illustrated in FIG. 10, at step 1002 one or more of the systems described herein may receive a 3D digital representation of an initial arrangement and a final arrangement of a plurality of teeth. For example, receiving module 804 may receive initial arrangement 822 and final arrangement 824.

At step 1004, one or more of the systems described herein may access a treatment database comprising data from a plurality of patient treatments, each of the plurality of treatments derived from a resistance model comprising lines of resistance at each of a plurality of stages. For example, planning module 806 may access a patient database, datastore or other data storage to retrieve treatment plan 826.

In some examples, the plurality of patient treatments may include treatments determined by applying an applied force system to a resistance model as described herein. Moreover, applying the applied force system may include applying a clinical treatment protocol to a three-dimensional (3D) model of the plurality of teeth.

In some examples, each of the plurality of patient treatments may include a plurality of stages derived from resistance model calculations. In addition, each of the plurality of stored patient treatments may include a plurality of stages with geometries derived from a CoR determined for each of the plurality of stages.

In some examples, each of the plurality of patient treatments may include any treatment as described herein, such as portions of treatment plan 826.

As illustrated in FIG. 10, at step 1006 one or more of the systems described herein may output 3D geometries of a plurality of stages in response to a correspondence between the initial arrangement, the final arrangement, and one or more of the plurality of patient treatments. For example, deriving module 810 may output appliance geometry 834 in response to a correspondence between initial arrangement 822, final arrangement 824, and treatment plan 826. The correspondence may be determined with a look up table or pick table identifying the one or more of the plurality of stored treatments.

The treatment database may comprise data related to the CoR determined as described herein, and in some embodiments, a plurality of treatment stages can be output without using modeling to determine the CoR of the plurality of treatment stages for the teeth to be treated, which can decrease computational time and resources. For example, the plurality of treatment stages can be output without finite element modeling of the CoR of the 3D digital representations of the input plurality of teeth at each of the plurality of intermediate stages, and the CoR values from the database can be used to determine the CoR for the treatment stages of the input teeth. In some embodiments, the treatment database comprises a sufficient number of treatments, such as 100 or more treatments, for example 1000 or more patients, such that the database can be configured to determine the treatment plan without performing CoR modeling calculations in order to determine the treatment plan from CoR derived treatment data comprising a plurality of stages as described herein.

In some embodiments, the database comprises data related to the CoR in order to improve the accuracy of the corresponding treatment identified from the database. The database may comprise on or more of whether or not the CoR exists, the orientation of the tooth, the orientation of the displacement to the tooth, demographic data such as age and gender, type of tooth (e.g. incisor, canine or molar), PDL thickness data, periodontal health, alveolar bone level, interface between alveolar bone and the tooth along the length of the root, mesial to distal width of the root near the alveolar crest, buccal to lingual width of the root near the alveolar crest, mesial to distal width of the root near the gum line, buccal to lingual width of the tooth near the gum line. Such data can be derived from measurements and images of the patient as described herein.

In some embodiments, the database comprises data related to changes to the alveolar bone during treatment. For example, the level of and location of the alveolar bone can change during treatment and this can be measured with imaging such as CBCT scan imaging at each of a plurality of treatment stages as described herein. Work in relation to the present disclosure suggests that alveolar bone can be resorbed and deposited during treatment in response to the applied forces, for example with activity of associated osteoblasts and osteoclasts that remodel the shape of the alveolar bone in which a tooth is located. In some embodiments, patient data from the roots of patient teeth from imaging studies of treated patients is stored in the database and used to determine the treatment plan for a patient. In some embodiments, once the database has been populated with treatments and related parameters as describe herein, data from the database is used to estimate parameters for a patient and plan the treatment without obtaining similar data from the patient to be treated. For example, root data from images of patients in the database can be used to estimate root data for the patient to be treated. In some embodiments, root data from CBCT scans stored in the database is used to estimate root data for the teeth of the patient to be treated without the patient to be treated undergoing CBCT scans, for example.

In some embodiments, the closest treatment in the database is identified, e.g. picked, in response to the initial and final teeth configurations of the input treatment dataset. Although reference is made to a look up table or a pick table to identify a prior treatment corresponding to a presently input initial and final configurations of the teeth to output a treatment plan, the treatment plan can be generated in many ways in response to the data from the database. In some embodiments, the treatment plan is generated with interpolation among parameters of the corresponding treatments from the database, for example interpolation among values of the prior treatments. Also, one or more components of the prior treatments can be identified as corresponding to the present treatment, such as the CoR of prior corresponding treatments, and these CoR values can be used to determine the CoR of one or more stages for the presently generated treatment plan. For example, the CoR value of an input tooth can be estimated from CoR values in the database, and this estimated CoR value for the input tooth can be used in conjunction with the force system 832 to determine the appliance geometry 834 for a stage of treatment, for example.

Figure 11:
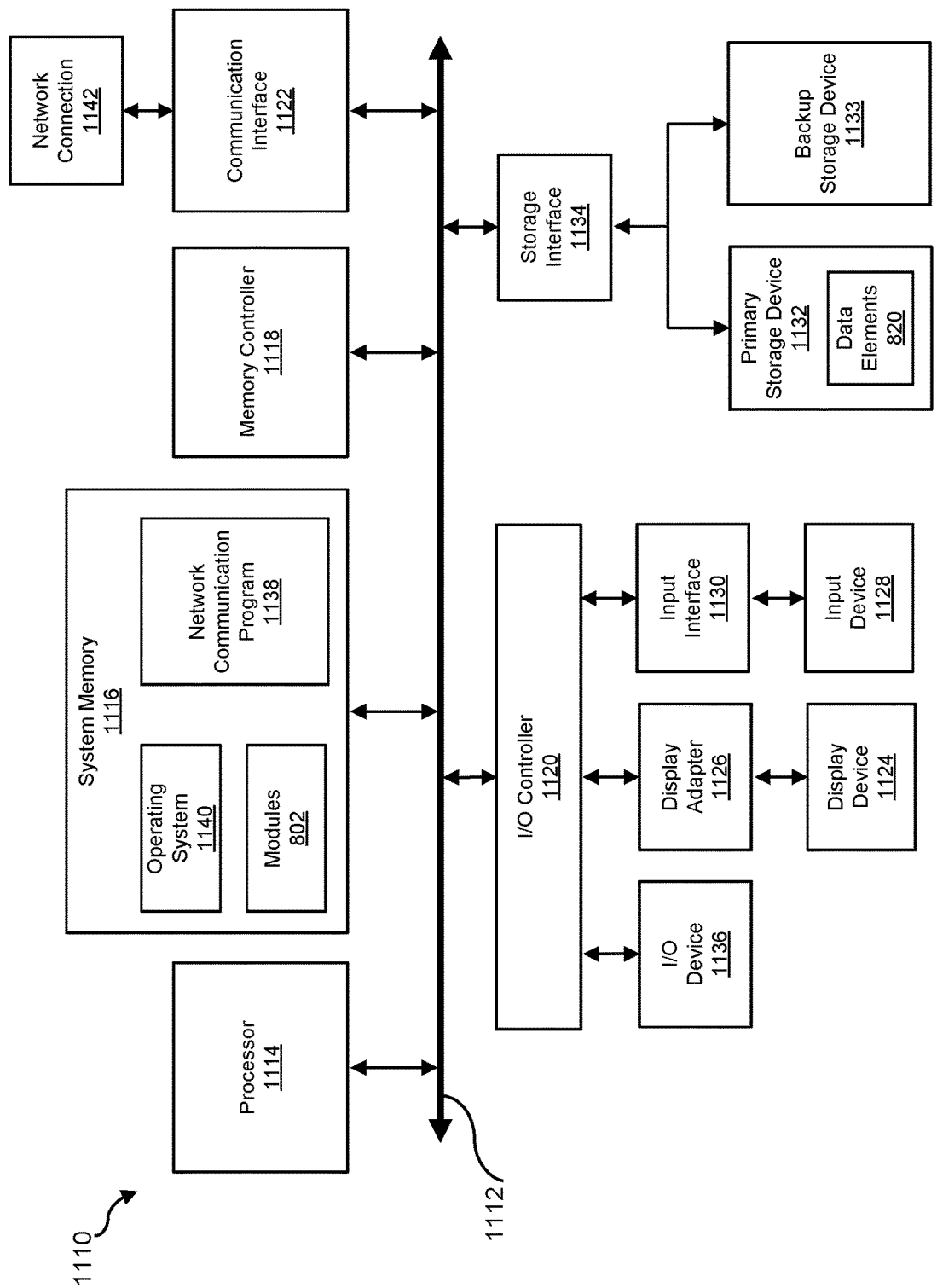
FIG. 11 shows a block diagram of an example computing system capable of implementing one or more embodiments described herein, in accordance with some embodiments.

FIG. 11 is a block diagram of an example computing system 1110 capable of implementing one or more of the embodiments described and/or illustrated herein. For example, all or a portion of computing system 1110 may perform and/or be a means for performing, either alone or in combination with other elements, one or more of the steps described herein (such as one or more of the steps illustrated in FIGS. 9 and/or 10). All or a portion of computing system 1110 may also perform and/or be a means for performing any other steps, methods, or processes described and/or illustrated herein.

Computing system 1110 broadly represents any single or multi-processor computing device or system capable of executing computer-readable instructions. Examples of computing system 1110 include, without limitation, workstations, laptops, client-side terminals, servers, distributed computing systems, handheld devices, or any other computing system or device. In its most basic configuration, computing system 1110 may include at least one processor 1114 and a system memory 1116.

Processor 1114 generally represents any type or form of physical processing unit (e.g., a hardware-implemented central processing unit) capable of processing data or interpreting and executing instructions. In some embodiments, processor 1114 may receive instructions from a software application or module. These instructions may cause processor 1114 to perform the functions of one or more of the example embodiments described and/or illustrated herein.

System memory 1116 generally represents any type or form of volatile or non-volatile storage device or medium capable of storing data and/or other computer-readable instructions. Examples of system memory 1116 include, without limitation, Random Access Memory (RAM), Read Only Memory (ROM), flash memory, or any other suitable memory device. Although not required, in some embodiments computing system 1110 may include both a volatile memory unit (such as, for example, system memory 1116) and a non-volatile storage device (such as, for example, primary storage device 1132, as described in detail below). In one example, one or more of modules 802 from FIG. 8 may be loaded into system memory 1116.

In some examples, system memory 1116 may store and/or load an operating system 1140 for execution by processor 1114. In one example, operating system 1140 may include and/or represent software that manages computer hardware and software resources and/or provides common services to computer programs and/or applications on computing system 1110. Examples of operating system 1140 include, without limitation, LINUX, JUNOS, MICROSOFT WINDOWS, WINDOWS MOBILE, MAC OS, APPLE'S IOS, UNIX, GOOGLE CHROME OS, GOOGLE'S ANDROID, SOLARIS, variations of one or more of the same, and/or any other suitable operating system.

In some embodiments, example computing system 1110 may also include one or more components or elements in addition to processor 1114 and system memory 1116. For example, as illustrated in FIG. 11, computing system 1110 may include a memory controller 1118, an Input/Output (I/O) controller 1120, and a communication interface 1122, each of which may be interconnected via a communication infrastructure 1112. Communication infrastructure 1112 generally represents any type or form of infrastructure capable of facilitating communication between one or more components of a computing device. Examples of communication infrastructure 1112 include, without limitation, a communication bus (such as an Industry Standard Architecture (ISA), Peripheral Component Interconnect (PCI), PCI Express (PCIe), or similar bus) and a network.

Memory controller 1118 generally represents any type or form of device capable of handling memory or data or controlling communication between one or more components of computing system 1110. For example, in some embodiments memory controller 1118 may control communication between processor 1114, system memory 1116, and I/O controller 1120 via communication infrastructure 1112.

I/O controller 1120 generally represents any type or form of module capable of coordinating and/or controlling the input and output functions of a computing device. For example, in some embodiments I/O controller 1120 may control or facilitate transfer of data between one or more elements of computing system 1110, such as processor 1114, system memory 1116, communication interface 1122, display adapter 1126, input interface 1130, and storage interface 1134.

As illustrated in FIG. 11, computing system 1110 may also include at least one display device 1124 coupled to I/O controller 1120 via a display adapter 1126. Display device 1124 generally represents any type or form of device capable of visually displaying information forwarded by display adapter 1126. Similarly, display adapter 1126 generally represents any type or form of device configured to forward graphics, text, and other data from communication infrastructure 1112 (or from a frame buffer, as known in the art) for display on display device 1124.

As illustrated in FIG. 11, example computing system 1110 may also include at least one input device 1128 coupled to I/O controller 1120 via an input interface 1130. Input device 1128 generally represents any type or form of input device capable of providing input, either computer or human generated, to example computing system 1110. Examples of input device 1128 include, without limitation, a keyboard, a pointing device, a speech recognition device, variations or combinations of one or more of the same, and/or any other input device.

Additionally or alternatively, example computing system 1110 may include additional I/O devices. For example, example computing system 1110 may include I/O device 1136. In this example, I/O device 1136 may include and/or represent a user interface that facilitates human interaction with computing system 1110. Examples of I/O device 1136 include, without limitation, a computer mouse, a keyboard, a monitor, a printer, a modem, a camera, a scanner, a microphone, a touchscreen device, variations or combinations of one or more of the same, and/or any other I/O device.

Communication interface 1122 broadly represents any type or form of communication device or adapter capable of facilitating communication between example computing system 1110 and one or more additional devices. For example, in some embodiments communication interface 1122 may facilitate communication between computing system 1110 and a private or public network including additional computing systems. Examples of communication interface 1122 include, without limitation, a wired network interface (such as a network interface card), a wireless network interface (such as a wireless network interface card), a modem, and any other suitable interface. In at least one embodiment, communication interface 1122 may provide a direct connection to a remote server via a direct link to a network, such as the Internet. Examples of the network include, without limitation, an intranet, a Wide Area Network (WAN), a Local Area Network (LAN), a Personal Area Network (PAN), the Internet, Power Line Communications (PLC), a cellular network (e.g., a Global System for Mobile Communications (GSM) network), portions of one or more of the same, variations or combinations of one or more of the same, and/or any other suitable network. Communication interface 1122 may also indirectly provide such a connection through, for example, a local area network (such as an Ethernet network), a personal area network, a telephone or cable network, a cellular telephone connection, a satellite data connection, or any other suitable connection.

In some embodiments, communication interface 1122 may also represent a host adapter configured to facilitate communication between computing system 1110 and one or more additional network or storage devices via an external bus or communications channel. Examples of host adapters include, without limitation, Small Computer System Interface (SCSI) host adapters, Universal Serial Bus (USB) host adapters, Institute of Electrical and Electronics Engineers (IEEE) 1394 host adapters, Advanced Technology Attachment (ATA), Parallel ATA (PATA), Serial ATA (SATA), and External SATA (eSATA) host adapters, Fibre Channel interface adapters, Ethernet adapters, or the like. Communication interface 1122 may also allow computing system 1110 to engage in distributed or remote computing. For example, communication interface 1122 may receive instructions from a remote device or send instructions to a remote device for execution.

In some examples, system memory 1116 may store and/or load a network communication program 1138 for execution by processor 1114. In one example, network communication program 1138 may include and/or represent software that enables computing system 1110 to establish a network connection 1142 with another computing system (not illustrated in FIG. 11) and/or communicate with the other computing system by way of communication interface 1122. In this example, network communication program 1138 may direct the flow of outgoing traffic that is sent to the other computing system via network connection 1142. Additionally or alternatively, network communication program 1138 may direct the processing of incoming traffic that is received from the other computing system via network connection 1142 in connection with processor 1114.

Although not illustrated in this way in FIG. 11, network communication program 1138 may alternatively be stored and/or loaded in communication interface 1122. For example, network communication program 1138 may include and/or represent at least a portion of software and/or firmware that is executed by a processor and/or Application Specific Integrated Circuit (ASIC) incorporated in communication interface 1122.

As illustrated in FIG. 11, example computing system 1110 may also include a primary storage device 1132 and a backup storage device 1133 coupled to communication infrastructure 1112 via a storage interface 1134. Storage devices 1132 and 1133 generally represent any type or form of storage device or medium capable of storing data and/or other computer-readable instructions. For example, storage devices 1132 and 1133 may be a magnetic disk drive (e.g., a so-called hard drive), a solid state drive, a floppy disk drive, a magnetic tape drive, an optical disk drive, a flash drive, or the like. Storage interface 1134 generally represents any type or form of interface or device for transferring data between storage devices 1132 and 1133 and other components of computing system 1110. In one example, data elements 820 from FIG. 8 may be stored and/or loaded in primary storage device 1132.

In some embodiments, storage devices 1132 and 1133 may be configured to read from and/or write to a removable storage unit configured to store computer software, data, or other computer-readable information. Examples of suitable removable storage units include, without limitation, a floppy disk, a magnetic tape, an optical disk, a flash memory device, or the like. Storage devices 1132 and 1133 may also include other similar structures or devices for allowing computer software, data, or other computer-readable instructions to be loaded into computing system 1110. For example, storage devices 1132 and 1133 may be configured to read and write software, data, or other computer-readable information. Storage devices 1132 and 1133 may also be a part of computing system 1110 or may be a separate device accessed through other interface systems.

Many other devices or subsystems may be connected to computing system 1110. Conversely, all of the components and devices illustrated in FIG. 11 need not be present to practice the embodiments described and/or illustrated herein. The devices and subsystems referenced above may also be interconnected in different ways from that shown in FIG. 11. Computing system 1110 may also employ any number of software, firmware, and/or hardware configurations. For example, one or more of the example embodiments disclosed herein may be encoded as a computer program (also referred to as computer software, software applications, computer-readable instructions, or computer control logic) on a computer-readable medium. The term "computer-readable medium," as used herein, generally refers to any form of device, carrier, or medium capable of storing or carrying computer-readable instructions. Examples of computer-readable media include, without limitation, transmission-type media, such as carrier waves, and non-transitory-type media, such as magnetic-storage media (e.g., hard disk drives, tape drives, and floppy disks), optical-storage media (e.g., Compact Disks (CDs), Digital Video Disks (DVDs), and BLU-RAY disks), electronic-storage media (e.g., solid-state drives and flash media), and other distribution systems.

The computer-readable medium containing the computer program may be loaded into computing system 1110. All or a portion of the computer program stored on the computer-readable medium may then be stored in system memory 1116 and/or various portions of storage devices 1132 and 1133. When executed by processor 1114, a computer program loaded into computing system 1110 may cause processor 1114 to perform and/or be a means for performing the functions of one or more of the example embodiments described and/or illustrated herein. Additionally or alternatively, one or more of the example embodiments described and/or illustrated herein may be implemented in firmware and/or hardware. For example, computing system 1110 may be configured as an Application Specific Integrated Circuit (ASIC) adapted to implement one or more of the example embodiments disclosed herein.

Figure 12:
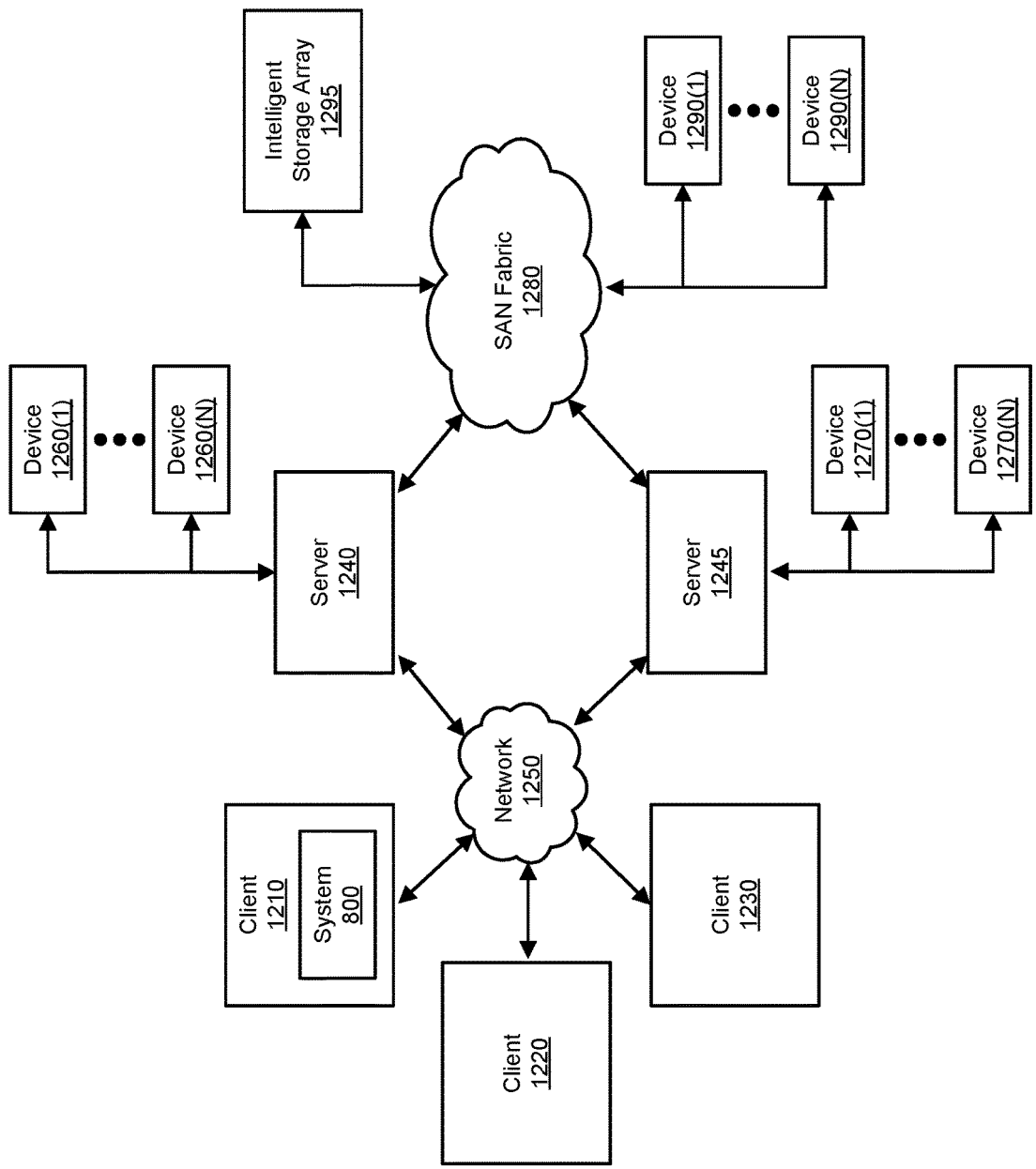
FIG. 12 shows a block diagram of an example computing network capable of implementing one or more of the embodiments described herein, in accordance with some embodiments.

FIG. 12 is a block diagram of an example network architecture 1200 in which client systems 1210, 1220, and 1230 and servers 1240 and 1245 may be coupled to a network 1250. As detailed above, all or a portion of network architecture 1200 may perform and/or be a means for performing, either alone or in combination with other elements, one or more of the steps disclosed herein (such as one or more of the steps illustrated in FIGS. 9 and/or 10). All or a portion of network architecture 1200 may also be used to perform and/or be a means for performing other steps and features set forth in the instant disclosure.

Client systems 1210, 1220, and 1230 generally represent any type or form of computing device or system, such as example computing system 1110 in FIG. 11. Similarly, servers 1240 and 1245 generally represent computing devices or systems, such as application servers or database servers, configured to provide various database services and/or run certain software applications. Network 1250 generally represents any telecommunication or computer network including, for example, an intranet, a WAN, a LAN, a PAN, or the Internet. In one example, client systems 1210, 1220, and/or 1230 and/or servers 1240 and/or 1245 may include all or a portion of system 800 from FIG. 8.

As illustrated in FIG. 12, one or more storage devices 1260(1)-(N) may be directly attached to server 1240. Similarly, one or more storage devices 1270(1)-(N) may be directly attached to server 1245. Storage devices 1260(1)-(N) and storage devices 1270(1)-(N) generally represent any type or form of storage device or medium capable of storing data and/or other computer-readable instructions. In some embodiments, storage devices 1260(1)-(N) and storage devices 1270(1)-(N) may represent Network-Attached Storage (NAS) devices configured to communicate with servers 1240 and 1245 using various protocols, such as Network File System (NFS), Server Message Block (SMB), or Common Internet File System (CIFS).

Servers 1240 and 1245 may also be connected to a Storage Area Network (SAN) fabric 1280. SAN fabric 1280 generally represents any type or form of computer network or architecture capable of facilitating communication between a plurality of storage devices. SAN fabric 1280 may facilitate communication between servers 1240 and 1245 and a plurality of storage devices 1290(1)-(N) and/or an intelligent storage array 1295. SAN fabric 1280 may also facilitate, via network 1250 and servers 1240 and 1245, communication between client systems 1210, 1220, and 1230 and storage devices 1290(1)-(N) and/or intelligent storage array 1295 in such a manner that devices 1290(1)-(N) and array 1295 appear as locally attached devices to client systems 1210, 1220, and 1230. As with storage devices 1260(1)-(N) and storage devices 1270(1)-(N), storage devices 1290(1)-(N) and intelligent storage array 1295 generally represent any type or form of storage device or medium capable of storing data and/or other computer-readable instructions.

In some embodiments, and with reference to example computing system 1110 of FIG. 11, a communication interface, such as communication interface 1122 in FIG. 11, may be used to provide connectivity between each client system 1210, 1220, and 1230 and network 1250. Client systems 1210, 1220, and 1230 may be able to access information on server 1240 or 1245 using, for example, a web browser or other client software. Such software may allow client systems 1210, 1220, and 1230 to access data hosted by server 1240, server 1245, storage devices 1260(1)-(N), storage devices 1270(1)-(N), storage devices 1290(1)-(N), or intelligent storage array 1295. Although FIG. 12 depicts the use of a network (such as the Internet) for exchanging data, the embodiments described and/or illustrated herein are not limited to the Internet or any particular network-based environment.

In at least one embodiment, all or a portion of one or more of the example embodiments disclosed herein may be encoded as a computer program and loaded onto and executed by server 1240, server 1245, storage devices 1260(1)-(N), storage devices 1270(1)-(N), storage devices 1290(1)-(N), intelligent storage array 1295, or any combination thereof. All or a portion of one or more of the example embodiments disclosed herein may also be encoded as a computer program, stored in server 1240, run by server 1245, and distributed to client systems 1210, 1220, and 1230 over network 1250.

As detailed above, computing system 1110 and/or one or more components of network architecture 1200 may perform and/or be a means for performing, either alone or in combination with other elements, one or more steps of an example method for virtual care.

While the foregoing disclosure sets forth various embodiments using specific block diagrams, flowcharts, and examples, each block diagram component, flowchart step, operation, and/or component described and/or illustrated herein may be implemented, individually and/or collectively, using a wide range of hardware, software, or firmware (or any combination thereof) configurations. In addition, any disclosure of components contained within other components should be considered example in nature since many other architectures can be implemented to achieve the same functionality.

In some examples, all or a portion of example system 800 in FIG. 8 may represent portions of a cloud-computing or network-based environment. Cloud-computing environments may provide various services and applications via the Internet. These cloud-based services (e.g., software as a service, platform as a service, infrastructure as a service, etc.) may be accessible through a web browser or other remote interface. Various functions described herein may be provided through a remote desktop environment or any other cloud-based computing environment.

In various embodiments, all or a portion of example system 800 in FIG. 8 may facilitate multi-tenancy within a cloud-based computing environment. In other words, the software modules described herein may configure a computing system (e.g., a server) to facilitate multi-tenancy for one or more of the functions described herein. For example, one or more of the software modules described herein may program a server to enable two or more clients (e.g., customers) to share an application that is running on the server. A server programmed in this manner may share an application, operating system, processing system, and/or storage system among multiple customers (i.e., tenants). One or more of the modules described herein may also partition data and/or configuration information of a multi-tenant application for each customer such that one customer cannot access data and/or configuration information of another customer.

According to various embodiments, all or a portion of example system 800 in FIG. 8 may be implemented within a virtual environment. For example, the modules and/or data described herein may reside and/or execute within a virtual machine. As used herein, the term "virtual machine" generally refers to any operating system environment that is abstracted from computing hardware by a virtual machine manager (e.g., a hypervisor). Additionally or alternatively, the modules and/or data described herein may reside and/or execute within a virtualization layer. As used herein, the term "virtualization layer" generally refers to any data layer and/or application layer that overlays and/or is abstracted from an operating system environment. A virtualization layer may be managed by a software virtualization solution (e.g., a file system filter) that presents the virtualization layer as though it were part of an underlying base operating system. For example, a software virtualization solution may redirect calls that are initially directed to locations within a base file system and/or registry to locations within a virtualization layer.

In some examples, all or a portion of example system 800 in FIG. 8 may represent portions of a mobile computing environment. Mobile computing environments may be implemented by a wide range of mobile computing devices, including mobile phones, tablet computers, e-book readers, personal digital assistants, wearable computing devices (e.g., computing devices with a head-mounted display, smartwatches, etc.), and the like. In some examples, mobile computing environments may have one or more distinct features, including, for example, reliance on battery power, presenting only one foreground application at any given time, remote management features, touchscreen features, location and movement data (e.g., provided by Global Positioning Systems, gyroscopes, accelerometers, etc.), restricted platforms that restrict modifications to system-level configurations and/or that limit the ability of third-party software to inspect the behavior of other applications, controls to restrict the installation of applications (e.g., to only originate from approved application stores), etc. Various functions described herein may be provided for a mobile computing environment and/or may interact with a mobile computing environment.

In addition, all or a portion of example system 800 in FIG. 8 may represent portions of, interact with, consume data produced by, and/or produce data consumed by one or more systems for information management. As used herein, the term "information management" may refer to the protection, organization, and/or storage of data. Examples of systems for information management may include, without limitation, storage systems, backup systems, archival systems, replication systems, high availability systems, data search systems, virtualization systems, and the like.

In some embodiments, all or a portion of example system 800 in FIG. 8 may represent portions of, produce data protected by, and/or communicate with one or more systems for information security. As used herein, the term "information security" may refer to the control of access to protected data. Examples of systems for information security may include, without limitation, systems providing managed security services, data loss prevention systems, identity authentication systems, access control systems, encryption systems, policy compliance systems, intrusion detection and prevention systems, electronic discovery systems, and the like.

The process parameters and sequence of steps described and/or illustrated herein are given by way of example only and can be varied as desired. For example, while the steps illustrated and/or described herein may be shown or discussed in a particular order, these steps do not necessarily need to be performed in the order illustrated or discussed. The various example methods described and/or illustrated herein may also omit one or more of the steps described or illustrated herein or include additional steps in addition to those disclosed.

A person of ordinary skill in the art will recognize that any process or method disclosed herein can be modified in many ways. The process parameters and sequence of the steps described and/or illustrated herein are given by way of example only and can be varied as desired. For example, while the steps illustrated and/or described herein may be shown or discussed in a particular order, these steps do not necessarily need to be performed in the order illustrated or discussed.

The various exemplary methods described and/or illustrated herein may also omit one or more of the steps described or illustrated herein or comprise additional steps in addition to those disclosed. Further, a step of any method as disclosed herein can be combined with any one or more steps of any other method as disclosed herein.

The processor as described herein can be configured to perform one or more steps of any method disclosed herein. Alternatively or in combination, the processor can be configured to combine one or more steps of one or more methods as disclosed herein.

Unless otherwise noted, the terms "connected to" and "coupled to" (and their derivatives), as used in the specification and claims, are to be construed as permitting both direct and indirect (i.e., via other elements or components) connection. In addition, the terms "a" or "an," as used in the specification and claims, are to be construed as meaning "at least one of" Finally, for ease of use, the terms "including" and "having" (and their derivatives), as used in the specification and claims, are interchangeable with and shall have the same meaning as the word "comprising.

The processor as disclosed herein can be configured with instructions to perform any one or more steps of any method as disclosed herein.

It will be understood that although the terms "first," "second," "third", etc. may be used herein to describe various layers, elements, components, regions or sections without referring to any particular order or sequence of events. These terms are merely used to distinguish one layer, element, component, region or section from another layer, element, component, region or section. A first layer, element, component, region or section as described herein could be referred to as a second layer, element, component, region or section without departing from the teachings of the present disclosure.

As used herein, the term "or" is used inclusively to refer items in the alternative and in combination.

As used herein, characters such as numerals refer to like elements.

The present disclosure includes the following numbered clauses.

Clause 1. A method of orthodontic treatment, comprising: receiving a 3D digital representation of an initial arrangement and a final arrangement of a plurality of teeth; determining a 3D treatment plan comprising a plurality of 3D stages for rearranging the plurality of teeth from the initial arrangement toward the final arrangement; determining, in accordance with the 3D treatment plan, an intended movement of at least one tooth for each of the plurality of stages; deriving, using a 3D resistance model, an applied force system for achieving the intended movement of the at least one tooth for each of the plurality of stages; and deriving 3D geometries of a plurality of oral appliances for the plurality of stages in response to the applied force system.

Clause 2. The method of clause 1, wherein the 3D resistance model comprises 3 lines of resistance of the at least one tooth at each of the plurality of stages and wherein the 3 lines of resistance change in response to forces from different directions at each of the plurality of stages.

Clause 3. The method of clause 2, wherein the applied force system is configured to apply a substantially translational force to the at least one tooth in response to the three lines of resistance and a moment to the at least one tooth in response to the three lines of resistance for each of the plurality of stages.

Clause 4. The method of clause 3, wherein the applied force system comprises a plurality of force vectors, the plurality of force vectors comprising a primary force vector and a resultant force vector to apply forces to the at least one tooth for at least one of the plurality of stages.

Clause 5. The method of clause 4, wherein the plurality of force vectors comprises three or more force vectors for each of the plurality of stages.

Clause 6. The method of clause 4, wherein the resultant force vector comprises a force from a power arm for application of a force at a location away from a surface of the at least one tooth to provide a moment to the at least one tooth.

Clause 7. The method of clause 2, wherein the three lines of resistance are determined with finite element modeling at each of the plurality of stages.

Clause 8. The method of clause 1, further comprising: determining whether the at least one tooth comprises a 3D center of resistance.

Clause 9. The method of clause 8, wherein the at least one tooth comprises the 3D center of resistance and the 3D center of resistance changes from a first stage of the plurality of stages to a second stage of the plurality of stages.

Clause 10. The method of clause 9, wherein the applied force system comprises a 3D force vector applied to the at least one tooth for each of the plurality of stages and wherein the 3D force vector changes in response to a change in the 3D center of resistance from the first stage to the second stage.

Clause 11. The method of clause 8, wherein the at least one tooth comprises the 3D center of resistance for a first plurality of stages and does not comprise the center of resistance for a second plurality of stages.

Clause 12. The method of clause 8, wherein the at least one tooth does not comprise the 3D center of resistance and the 3D resistance model comprises 3 axes of resistance and wherein the 3 axes of resistance are determined for the at least one tooth for each of the plurality of stages.

Clause 13. The method of clause 12, wherein a 3D force vector to move the at least one tooth is determined at each of the plurality of stages in response to the three axes of resistance of the stage and wherein a 3D moment to the at least one tooth is determined in response to the three axes of resistance at each of the plurality of stages.

Clause 14. The method of clause 13, wherein the 3D force vector to move the at least one tooth includes a 3D force vector to rotate the at least one tooth.

Clause 15. The method of clause 13, wherein the 3D force vector to move the at least one tooth includes a 3D force vector to translate the at least one tooth.

Clause 16. The method of clause 13, wherein the 3D force vector to move the at least one tooth includes a 3D force vector to rotate and translate the at least one tooth.

Clause 17. The method of clause 1, further comprising: calculating the force system in response to the intended movement; and calculating a resistance model representing the at least one tooth for providing the force system on the at least one tooth at each of the plurality of stages.

Clause 18. The method of clause 17, wherein the intended movement is at least one of rotation and translation.

Clause 19. The method of clause 1, wherein the resistance model further comprises a translational force and a moment to be applied to the at least one tooth for each of the plurality of stages.

Clause 20. The method of clause 18, wherein each of the plurality of oral appliances comprises a power arm for applying the translational force and the moment to be applied to the at least one tooth for each of the plurality of stages.

Clause 21. The method of clause 1, wherein the resistance model comprises a center of resistance for the at least one tooth.

Clause 22. The method of clause 1, wherein the 3D digital representation comprises a three dimensional (3D) model of the plurality of teeth.

Clause 23. The method of clause 21, wherein acquiring the 3D model comprises scanning the plurality of teeth.

Clause 24. The method of clause 21, wherein deriving the applied force system comprises applying the treatment plan to the 3D model to simulate rearranging the plurality of teeth from the initial arrangement to the final arrangement.

Clause 25. The method of clause 1, wherein parameters of the resistance model are determined at each of the plurality of stages with finite element modeling (FEM").

Clause 26. The method of clause 1, further comprising storing, in a database, the 3D digital representation of the initial arrangement and a 3D digital representation the final arrangement of the plurality of teeth after receiving the 3D digital representation.

Clause 27. The method of clause 1, wherein the 3D digital representation comprises one or more of optical scan data or CBCT scan data.

Clause 28. The method of clause 1, wherein the 3D resistance model comprises one or more of a linear 3D resistance model or a non-linear 3D resistance model.

Clause 29. The method of clause 1, wherein the 3D resistance model comprises a parameter selected from the group consisting of a PDL Young's modulus, a PDL thickness, a PDL Poisson's ratio and a Bone Young's modulus.

Clause 30. The method of clause 28, wherein the PDL Young's modulus is within a range from 0.05 to $10^6$ MPa, the PDL thickness within a range from 0.1 mm to 4 mm, the Poisson's ratio is within a range from −1 to 0.5, the Poisson's ratio is within a range from 0 to 0.49, or the Bone Young's modulus is at least 2000 MPa.

Clause 31. The method of clause 28, wherein the parameter comprises the Poisson's ratio, the Poisson's ratio within a range from 0 to 0.49.

Clause 32. The method of clause 1, further comprising fabricating the plurality of oral appliances using the derived geometries.

Clause 33. The method of clause 31, wherein fabricating the oral appliance further comprises converting the derived geometry into instructions for fabricating the appliance.

Clause 34. The method of clause 31, wherein fabricating the oral appliance further comprises using one or more of thermoforming and direct fabrication.

Clause 35. A method of orthodontic treatment planning comprising: receiving a 3D digital representation of an initial arrangement and a final arrangement of a plurality of teeth; accessing a treatment database comprising data from a plurality of patient treatments, each of the plurality of treatments derived from a resistance model comprising lines of resistance at each of a plurality of stages; and outputting 3D geometries of a plurality of stages in response to a correspondence between the initial arrangement, the final arrangement, and one or more of the plurality of patient treatments.

Clause 36. The method of clause 34, wherein the plurality of patient treatments comprise treatments determined by applying an applied force system to a resistance model.

Clause 37. The method of clause 34, wherein each of the plurality of patient treatments comprises a plurality of stages derived from resistance model calculations.

Clause 38. The method of clause 34, wherein each of the plurality of patient treatments comprises a plurality of stages with geometries derived from a center of resistance determined for each of the plurality of stages.

Clause 39. The method of clause 34, wherein the correspondence is determined with a look up table identifying the one or more of the plurality of patient treatments.

Clause 40. The method of clause 35, wherein applying the applied force system further comprises applying a clinical treatment protocol to a three-dimensional (3D) model of the plurality of teeth.

Clause 41. The method of clause 34, wherein each of the plurality of patient treatments comprises a treatment as in any one of clauses 1 to 33.

Clause 42. A system for orthodontic treatment comprising: a processor; and memory comprising a tangible medium and including instructions that when executed by the processor cause the system to carry out a method comprising: receiving a 3D digital representation of an initial arrangement and a final arrangement of a plurality of teeth; determining a 3D treatment plan comprising a plurality of 3D stages for rearranging the plurality of teeth from the initial arrangement toward the final arrangement; determining, in accordance with the 3D treatment plan, an intended movement of at least one tooth for each of the plurality of stages; deriving, using a 3D resistance model, an applied force system for achieving the intended movement of the at least one tooth for each of the plurality of stages; and deriving 3D geometries of a plurality of oral appliances for the plurality of stages in response to the applied force system.

Clause 43. The system of clause 42, wherein the 3D resistance model comprises 3 lines of resistance of the at least one tooth at each of the plurality of stages and wherein the 3 lines of resistance change in response to forces from different directions at each of the plurality of stages.

Clause 44. The system of clause 43, wherein the applied force system is configured to apply a substantially translational force to the at least one tooth in response to the three lines of resistance and a moment to the at least one tooth in response to the three lines of resistance for each of the plurality of stages.

Clause 45. The system of clause 44, wherein the applied force system comprises a plurality of force vectors, the plurality of force vectors comprising a primary force vector and a resultant force vector to apply forces to the at least one tooth for at least one of the plurality of stages.

Clause 46. The system of clause 45, wherein the plurality of force vectors comprises three or more force vectors for each of the plurality of stages.

Clause 47. The system of clause 45, wherein the resultant force vector comprises a force from a power arm for application of a force at a location away from a surface of the at least one tooth to provide a moment to the at least one tooth.

Clause 48. The system of clause 43, wherein the three lines of resistance are determined with finite element modeling at each of the plurality of stages.

Clause 49. The system of clause 42, the method further comprises: determining whether the at least one tooth comprises a 3D center of resistance.

Clause 50. The system of clause 49, wherein the at least one tooth comprises the 3D center of resistance and the 3D center of resistance changes from a first stage of the plurality of stages to a second stage of the plurality of stages.

Clause 51. The system of clause 50, wherein the applied force system comprises a 3D force vector applied to the at least one tooth for each of the plurality of stages and wherein the 3D force vector changes in response to a change in the 3D center of resistance from the first stage to the second stage.

Clause 52. The system of clause 49, wherein the at least one tooth comprises the 3D center of resistance for a first plurality of stages and does not comprise the center of resistance for a second plurality of stages.

Clause 53. The system of clause 49, wherein the at least one tooth does not comprise the 3D center of resistance and the 3D resistance model comprises 3 axes of resistance and wherein the 3 axes of resistance are determined for the at least one tooth for each of the plurality of stages.

Clause 54. The system of clause 53, wherein a 3D force vector to move the at least one tooth is determined at each of the plurality of stages in response to the three axes of resistance of the stage and wherein a 3D moment to the at least one tooth is determined in response to the three axes of resistance at each of the plurality of stages.

Clause 55. The system of clause 54, wherein the 3D force vector to move the at least one tooth includes a 3D force vector to rotate the at least one tooth.

Clause 56. The system of clause 54, wherein the 3D force vector to move the at least one tooth includes a 3D force vector to translate the at least one tooth.

Clause 57. The system of clause 54, wherein the 3D force vector to move the at least one tooth includes a 3D force vector to rotate and translate the at least one tooth.

Clause 58. The system of clause 42, the method further comprises: calculating the force system in response to the intended movement; and calculating a resistance model representing the at least one tooth for providing the force system on the at least one tooth at each of the plurality of stages.

Clause 59. The system of clause 58, wherein the intended movement is at least one of rotation and translation.

Clause 60. The system of clause 42, wherein the resistance model further comprises a translational force and a moment to be applied to the at least one tooth for each of the plurality of stages.

Clause 61. The system of clause 59, wherein each of the plurality of oral appliances comprises a power arm for applying the translational force and the moment to be applied to the at least one tooth for each of the plurality of stages.

Clause 62. The system of clause 42, wherein the resistance model comprises a center of resistance for the at least one tooth.

Clause 63. The system of clause 42, wherein the 3D digital representation comprises a three dimensional (3D) model of the plurality of teeth.

Clause 64. The system of clause 62, wherein acquiring the 3D model comprises scanning the plurality of teeth.

Clause 65. The system of clause 62, wherein deriving the applied force system comprises applying the treatment plan to the 3D model to simulate rearranging the plurality of teeth from the initial arrangement to the final arrangement.

Clause 66. The system of clause 42, wherein parameters of the resistance model are determined at each of the plurality of stages with finite element modeling (FEM").

Clause 67. The system of clause 42, where in the method further comprises storing, in a database, the 3D digital representation of the initial arrangement and a 3D digital representation the final arrangement of the plurality of teeth after receiving the 3D digital representation.

Clause 68. The system of clause 42, wherein the 3D digital representation comprises one or more of optical scan data or CBCT scan data.

Clause 69. The system of clause 42, wherein the 3D resistance model comprises one or more of a linear 3D resistance model or a non-linear 3D resistance model.

Clause 70. The system of clause 42, wherein the 3D resistance model comprises a parameter selected from the group consisting of a PDL Young's modulus, a PDL thickness, a PDL Poisson's ratio and a Bone Young's modulus.

Clause 71. The system of clause 69, wherein the PDL Young's modulus is within a range from 0.05 to $10^6$ MPa, the PDL thickness within a range from 0.1 mm to 4 mm, the Poisson's ratio is within a range from −1 to 0.5, the Poisson's ratio is within a range from 0 to 0.49, or the Bone Young's modulus is at least 2000 MPa.

Clause 72. The system of clause 69, wherein the parameter comprises the Poisson's ratio, the Poisson's ratio within a range from 0 to 0.49.

Clause 73. The system of clause 42, further comprising fabricating the plurality of oral appliances using the derived geometries.

Clause 74. The system of clause 72, wherein fabricating the oral appliance further comprises converting the derived geometry into instructions for fabricating the appliance.

Clause 75. The system of clause 72, wherein fabricating the oral appliance further comprises using one or more of thermoforming and direct fabrication.

Clause 76. A system of orthodontic treatment planning comprising: a processor; and memory comprising a tangible medium and including instructions that when executed by the processor cause the system to carry out a method comprising: receiving a 3D digital representation of an initial arrangement and a final arrangement of a plurality of teeth; accessing a treatment database comprising data from a plurality of patient treatments, each of the plurality of treatments derived from a resistance model comprising lines of resistance at each of a plurality of stages; and outputting 3D geometries of a plurality of stages in response to a correspondence between the initial arrangement, the final arrangement, and one or more of the plurality of patient treatments.

Clause 77. The system of clause 76, wherein the plurality of patient treatments comprise treatments determined by applying an applied force system to a resistance model.

Clause 78. The system of clause 76, wherein each of the plurality of patient treatments comprises a plurality of stages derived from resistance model calculations.

Clause 79. The system of clause 76, wherein each of the plurality of patient treatments comprises a plurality of stages with geometries derived from a center of resistance determined for each of the plurality of stages.

Clause 80. The system of clause 76, wherein the correspondence is determined with a look up table identifying the one or more of the plurality of patient treatments.

Clause 81. The method of clause 77, wherein applying the applied force system further comprises applying a clinical treatment protocol to a three-dimensional (3D) model of the plurality of teeth.

Embodiments of the present disclosure have been shown and described as set forth herein and are provided by way of example only. One of ordinary skill in the art will recognize numerous adaptations, changes, variations and substitutions without departing from the scope of the present disclosure. Several alternatives and combinations of the embodiments disclosed herein may be utilized without departing from the scope of the present disclosure and the inventions disclosed herein. Therefore, the scope of the presently disclosed inventions shall be defined solely by the scope of the appended claims and the equivalents thereof.

What is claimed is:

1. A method of orthodontic treatment, comprising:
receiving a 3D digital representation of an initial arrangement and a final arrangement of a plurality of teeth;
generating a 3D treatment plan comprising a plurality of 3D models of teeth for rearranging the plurality of teeth from the initial arrangement toward the final arrangement in a plurality of stages of treatment;
determining, in accordance with the 3D treatment plan, an intended movement of at least one tooth for each of the plurality of stages;
deriving, using a 3D resistance model, an applied force system for achieving the intended movement of the at least one tooth for each of the plurality of stages, wherein the 3D resistance model comprises three lines of resistance of the at least one tooth at each of the plurality of stages, wherein the three lines of resistance are determined based on forces at each of the plurality of stages, wherein the three lines of resistance change in response to forces from different directions at each of the plurality of stages, and deriving the 3D resistance model includes
determining whether the at least one tooth comprises a 3D center of resistance based on an intersection or lack thereof of the three lines of resistance; and
generating a plurality of oral appliances for the plurality of stages of treatment based on the derived applied force system.

2. The method of claim 1, wherein the applied force system is configured to apply a substantially translational force to the at least one tooth in response to the three lines of resistance and a moment to the at least one tooth in response to the three lines of resistance for each of the plurality of stages.

3. The method of claim 2, wherein the applied force system comprises a plurality of force vectors, the plurality of force vectors comprising a primary force vector and a resultant force vector to apply the forces to the at least one tooth for at least one of the plurality of stages.

4. The method of claim 3, wherein the plurality of force vectors comprises three or more force vectors for each of the plurality of stages.

5. The method of claim 3, wherein the resultant force vector comprises a force from a power arm for application of a force at a location away from a surface of the at least one tooth to provide a moment to the at least one tooth.

6. The method of claim 1, wherein the three lines of resistance are determined with finite element modeling at each of the plurality of stages.

7. The method of claim 1, wherein the at least one tooth comprises the 3D center of resistance and the 3D center of resistance changes from a first stage of the plurality of stages to a second stage of the plurality of stages.

8. The method of claim 7, wherein the applied force system comprises a 3D force vector applied to the at least one tooth for each of the plurality of stages and wherein the 3D force vector changes in response to a change in the 3D center of resistance from the first stage to the second stage.

* * * * *